US012582444B2

(12) United States Patent
    Postole et al.

(10) Patent No.:  US 12,582,444 B2
(45) Date of Patent:      Mar. 24, 2026

(54) MEDICAL DEVICE

(71) Applicant: Arbutus Medical Inc., Vancouver (CA)

(72) Inventors: Radu Postole, Vancouver (CA);
               Michael Cancilla, Vancouver (CA);
               John Kodosky, Vancouver (CA)

(73) Assignee: Arbutus Medical Inc., Vancouver (CA)

( * ) Notice:   Subject to any disclaimer, the term of this
               patent is extended or adjusted under 35
               U.S.C. 154(b) by 4 days.

(21) Appl. No.: 18/746,299

(22) Filed:     Jun. 18, 2024

(65)            Prior Publication Data

US 2024/0423674 A1      Dec. 26, 2024

Related U.S. Application Data

(60) Provisional application No. 63/509,296, filed on Jun.
     21, 2023.

(51) Int. Cl.
     *A61B 17/66*       (2006.01)
     *A61B 17/00*       (2006.01)
     *A61B 17/64*       (2006.01)
(52) U.S. Cl.
     CPC .......... *A61B 17/66* (2013.01); *A61B 17/6458*
               (2013.01); *A61B 2017/00486* (2013.01)
(58) Field of Classification Search
     CPC ................ A61B 17/66; A61B 17/6458; A61B
                    2017/00486; A61B 17/6408; A61B
                                17/6441; A61F 5/042
     See application file for complete search history.

(56)            References Cited

U.S. PATENT DOCUMENTS 1,363,114  A  *  12/1920  Hawley .............. A61B 17/6408
                                                      602/37
     1,952,750  A  *   3/1934  Gailey ................. A63B 21/023
                                                     482/125
     2,024,325  A  *  12/1935  Allen ................. A61B 17/6408
                                                     606/56
     2,204,266  A  *   6/1940  Wilcox .............. A61B 17/6408
                                                      5/624
     2,301,534  A  *  11/1942  Goodwin .............. A61F 5/0585
                                                     602/40
     4,350,153  A  *   9/1982  Borschneck .......... A61F 5/0585
                                                     602/40

(Continued)

FOREIGN PATENT DOCUMENTS

CN      203988545       12/2014
     CN      204169967        2/2015
                     (Continued)

OTHER PUBLICATIONS

International Search Report and Written Opinion issued for PCT/
IB2024/055946 on Sep. 5, 2024.
                     (Continued)

*Primary Examiner* — Tarla R Patel
(74) *Attorney, Agent, or Firm* — Foley & Lardner LLP

(57)            ABSTRACT
The present disclosure is directed to a medical device. The
medical device can include a body having a first extension
and having a second extension. The first extension can have
a first adapter and the second extension can have a second
adapter. The first adapter and the second adapter can couple
with at least one tensioning assembly to cause the body to
pivot from a first position to a second position.

20 Claims, 23 Drawing Sheets

(56) References Cited

U.S. PATENT DOCUMENTS

| | | | | | |
|---|---|---|---|---|---|
| 4,501,267 | A | * | 2/1985 | Pecheux | A61F 5/04 606/59 |
| 5,162,039 | A | * | 11/1992 | Dahners | A61F 5/04 602/23 |
| 5,290,220 | A | * | 3/1994 | Guhl | A61G 13/12 602/33 |
| 5,669,908 | A | * | 9/1997 | Gracilla | A61F 5/04 606/56 |
| 10,973,673 | B1 | | 4/2021 | Skraber | |
| 11,395,680 | B2 | * | 7/2022 | Chen | A61B 17/8866 |
| 2004/0092854 | A1 | * | 5/2004 | D'Amico | A61H 1/0218 602/32 |
| 2009/0105710 | A1 | * | 4/2009 | Saltzman | A61F 5/042 606/90 |
| 2009/0306567 | A1 | * | 12/2009 | Meyer | A61H 1/0218 602/33 |
| 2021/0307949 | A1 | * | 10/2021 | Ganti | A63B 21/065 |
| 2021/0338470 | A1 | * | 11/2021 | Nisivoccia | A61F 5/055 |

FOREIGN PATENT DOCUMENTS

| | | | | |
|---|---|---|---|---|
| CN | 106859829 | | 6/2017 | |
| CN | 110537964 | A * | 12/2019 | A61B 17/66 |
| CN | 110584859 | | 12/2019 | |
| CN | 210408711 | | 4/2020 | |
| DE | 20 2016 005 423 | | 12/2016 | |

OTHER PUBLICATIONS

BioAccess Traction Pin Kit (1 page) dated Aug. 31, 2015 https://www.youtube.com/watch?v=3g-g8PgVYpk.

BioAccess Traction Pin Kit (accessed Apr. 10, 2024) https://www.bioaccess.com/product_traction_pin_kit.html.

Preliminary Report on Patentability on PCT/IB2024/055946 dated Jan. 2, 2026.

* cited by examiner

300

135

135

125

405

125

410

105

155

160

165

170

120

130

120

910

905

1800

1900

MEDICAL DEVICE

CROSS-REFERENCE TO RELATED APPLICATIONS

This application claims the benefit of and priority to U.S. Provisional Patent Application No. 63/509,296, filed Jun. 21, 2023, the entire disclosure of which is incorporated by reference herein.

BACKGROUND

Various devices can be used to assist with the healing of bones, muscles, ligaments, or tendons in a body.

SUMMARY

At least one aspect is directed to a medical device. The medical device can include a body having a first extension and having a second extension. The first extension can have a first adapter and the second extension can have a second adapter. The first adapter and the second adapter can couple with at least one tensioning assembly to cause the body to pivot from a first position to a second position.

At least one aspect is directed to a method. The method can include providing a medical device including a body having a first extension and having a second extension. The first extension can have a first adapter and the second extension can have a second adapter. The method can include coupling the first adapter and the second adapter with at least one tensioning assembly. The method can include applying a force to the at least one tensioning assembly to cause the body to pivot from a first position to a second position.

At least one aspect is directed to an adapter. The adapter can include a first portion that can couple with a body of a medical device and a second portion that can couple with a tensioning assembly. The adapter can cause the body to pivot responsive to a force applied to the tensioning assembly.

At least one aspect is directed to a method. The method can include providing a medical device. The medical device can include a body having a first extension and having a second extension. The first extension can have a first adapter and the second extension can have a second adapter. The first adapter and the second adapter can couple with at least one tensioning assembly to cause the body to pivot from a first position to a second position.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Following below are more detailed descriptions of various concepts related to, and implementations of, methods, apparatuses, and systems of medical devices. The various concepts introduced above and discussed in greater detail below may be implemented in any of numerous ways.

Traction bows, which can be referred to herein as k-bows, can include medical devices that can engage with various components to aid medical professions during various medical operations or procedures, including surgery. The present disclosure generally relates to systems and methods for providing a medical device that can facilitate supporting one or more bones, muscles, or ligaments. For example, the present disclosure generally relates to a medical device (e.g., a k-bow) that can engage with a pin that protrudes through a portion of a bone or another component. The medical device can include a body having a first end, a second end, and two extensions extending between the first and second ends. Each of the extensions can couple with an adapter. The adapters can protrude at an angle from the extensions and can couple with at least a portion of a tensioning assembly to facilitate pivoting the body of the medical device when a force is applied to the tensioning assembly. For example, the adapters can facilitate pivoting the body from a first position to a second position such that the body does not contact an external body part of a patient using the medical device.

The present disclosure includes several advantages. For example, the present disclosure provides a medical device that may cause little or no pain, discomfort, or irritation for a patient using the medical device. Further, the medical device allows the body of the medical device to be oriented at an upward angled direction from a patient while being easy to install and easy to manufacture. Additionally, the medical device facilitates reducing or eliminating contact between the medical device and a patient (e.g., to reduce or eliminate the chance of developing pressure ulcers) with a pin extending through a portion of the patient's bone, which facilitates reducing pain and the chance of damage to the patient as opposed to using a pin of a larger diameter. Moreover, the medical device can pivot off a patient's body such that the applied force can be directly in line with the patient's leg (e.g., horizontal with a hospital bed), which may be preferred in many situations as opposed to the force being applied in an upward direction, to direct the medical device off of a leg or other body part of the patient. The medical device may also prevent the need for using a customized bed incorporating a traction frame, which may be needed to run a rope over a pulley. This may be preferred because it can be universally applied to any bed or stretcher which speeds up patient care and reduces need for patient transfer into a new bed.

Figure 1:
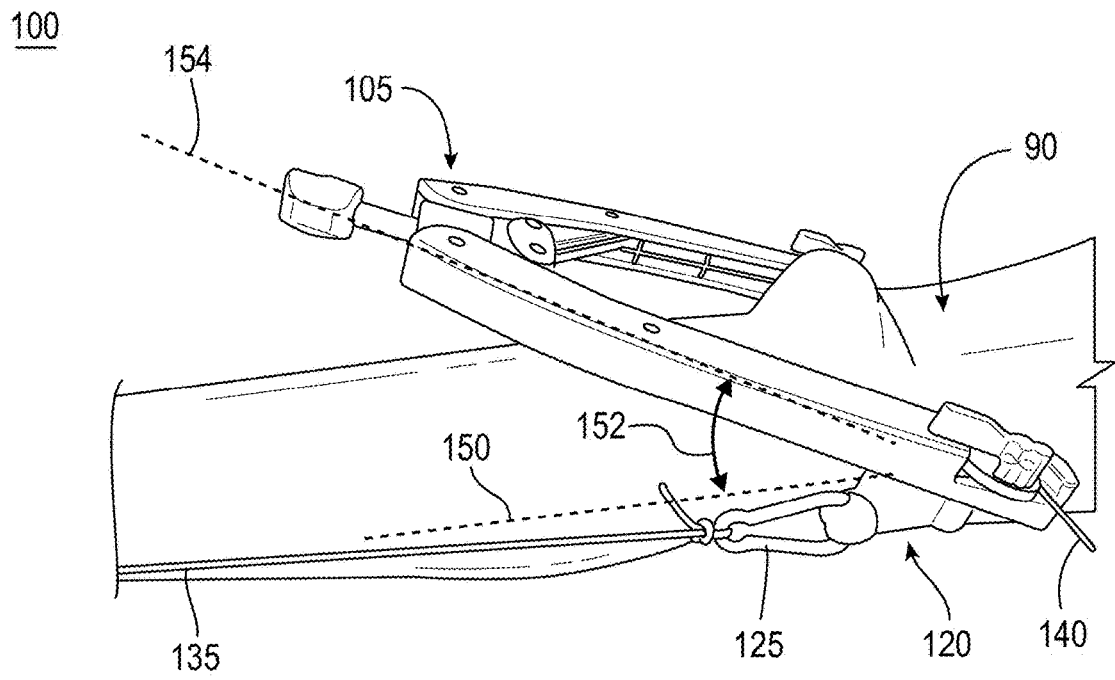
FIG. 1 is an example perspective view of a medical device system in an activated position, in accordance with implementations.
Figure 2:
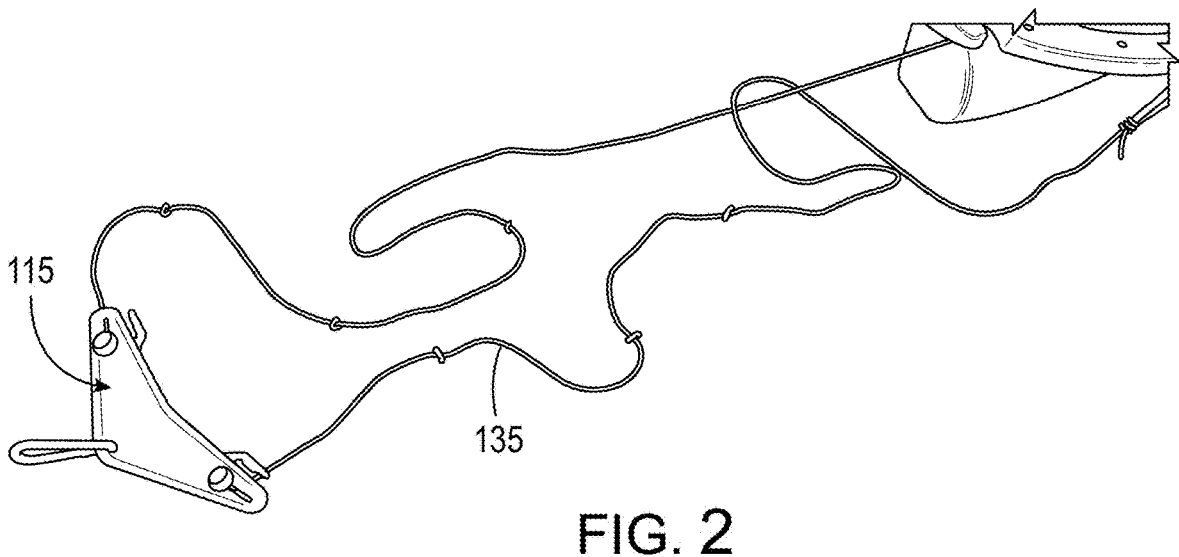
FIG. 2 is an example perspective view of a portion of the medical device system of FIG. 1, in accordance with implementations.

FIG. 1 depicts an example perspective view of a system (e.g., a medical device system) 100 and FIG. 2 depicts an example perspective view of a portion of the system 100, according to an example. The medical device system 100 can be used in one or more medical settings. For example, the medical device system 100 can facilitate healing a patient, the medical device system 100 can facilitate one or more medical professionals during operations or other activities, or the medical device system 100 can be used in various other applications. For example, the medical device system 100 can be used for a patient 90 with a fractured hip, femur, pelvis, or other bone. The medical device system 100 can be used to affix traction with a bone component (e.g., a pin, a wire, or another component).

The medical device system 100 can include a medical device 105. The medical device 105 can include a device to prevent, correct, or treat a medical condition, or to restore, correct, or modify a structure or function of a patient or other person, mammal, or animal. The medical device 105 can include at least one component (e.g., a pin 140) that can couple with a portion of a patient 90. For example, the pin 140 can extend through a portion of a bone of the patient 90. As described herein, the medical device 105 can include at least one adapter 120. The adapter 120 can couple with at least a portion of at least one tensioning assembly 300 (e.g., one or more of at least one connector 125, at least one line 135 (rope, string, wire, or other lines), at least one spreader bar 115, at least one weight 405 depicted in at least FIG.

4A-G, or one or more additional or alternative components described herein capable of applying a force to the adapter 120). For example, each adapter 120 can couple with a corresponding connector 125 (e.g., a first connector 125 and a second connector 125). Each connector 125 can couple with a corresponding line 135 or a portion of a line 135. The connector 125 can be or can include one or more clips, clamps, hooks, or other connectors. One or more of the adapters 120 can couple directly with the line 135 without the use of the connector 125.

Figure 3:
FIG. 3 is an example front view of a portion of a tensioning assembly of the medical device system of FIG. 1, in accordance with implementations.
Figure 3:
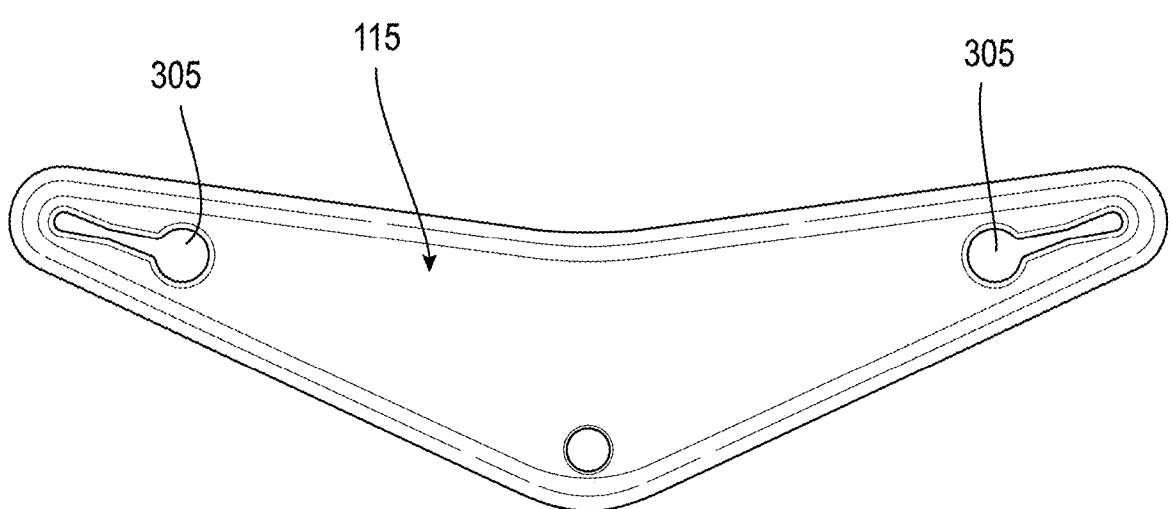

FIG. 3 depicts an example front view of a portion of an example tensioning assembly 300, the spreader bar 115. The spreader bar 115 can include at least one opening 305 that can receive a portion of the line(s) 135. The openings 305 can be sized, shaped, or configured to lock the line 135 in position (e.g., at a knot formed in the line 135) such that a force applied to the spreader bar 115 applies a force to the line 135. The spreader bar 115 can be a variety of shapes or sizes. For example, the spreader bar 115 can include a bowed shape (e.g., a boomerang-like shape, a bent cantilever shape) to facilitate preventing buckling or bending of the bar 115 when a force is applied to the bar 115. The spreader bar 115 can include a variety of other shapes including, but not limited to, a triangular shape, a square shape, an asymmetrical shape, or another type of shape. The spreader bar 115 can be about 5-15 inches (e.g., 6-12 inches, 12-40 cm) in length along a longest axis of the spreader bar 115, or the spreader bar 115 can be significantly greater or lesser in length (e.g., less than 5 inches, greater than 15 inches).

FIGS. 4A-4G depict example schematics of various examples of the tensioning assembly 300. For example, the one or more lines 135 can additionally or alternatively couple with a weight 405 (e.g., about 10% of a patient's body weight, about 10-30 lbs. about 20 lbs., or more or less weight) to apply a force to the lines 135 (e.g., with or in addition to the spreader bar 115). For example, the weight 405 can couple with the line 135 or with the spreader bar 115 (e.g., through one or more connectors 125). The bar 115 itself can include a weight 405 such that the bar 115 and at least one weight 405 are monolithic. The tensioning assembly 300 can include a pulley system coupled with the adapter 120 to at least partially store the line 135 such that the line 135 can be pulled out of the pulley.

Figure 4A:
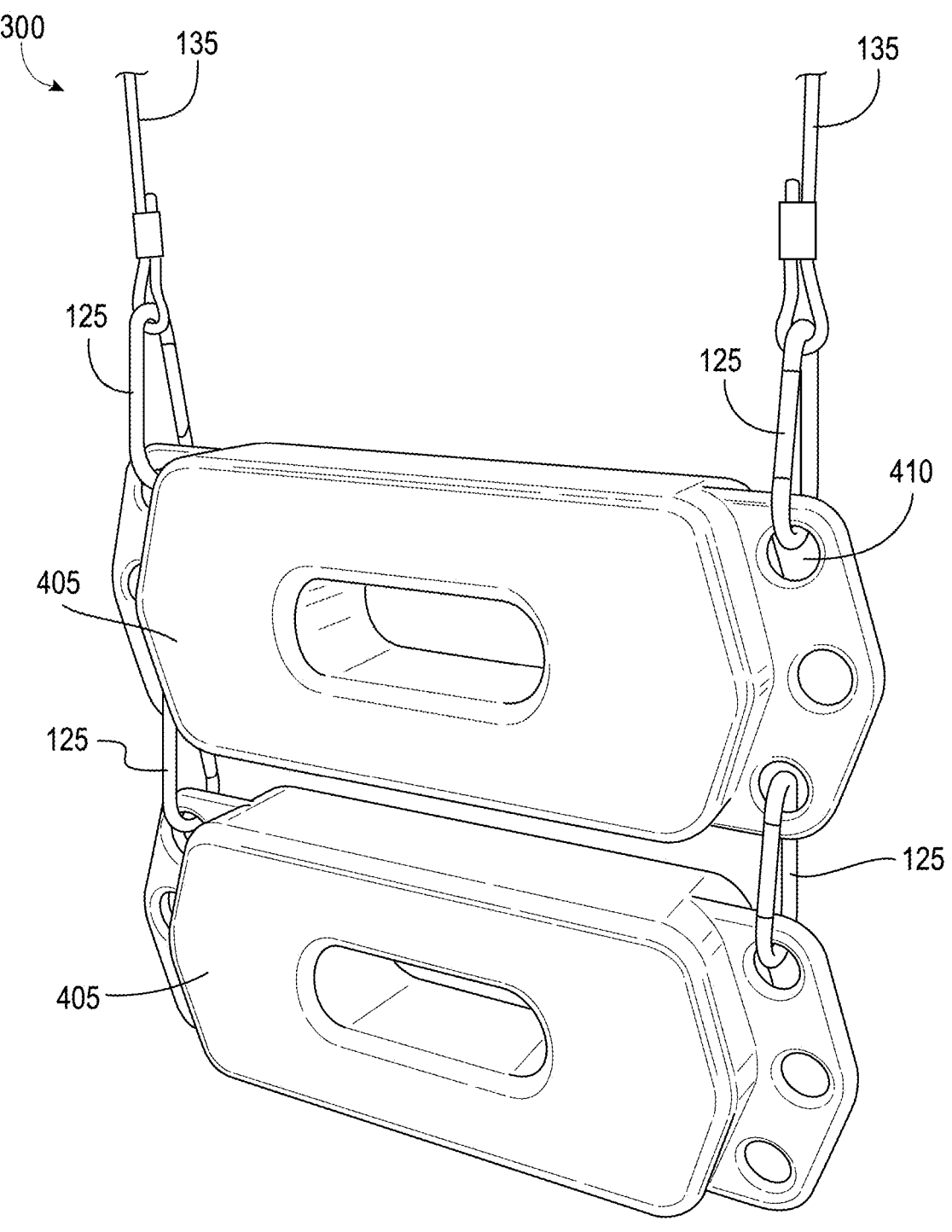
FIGS. 4A-4G are example schematics of a portion of a tensioning assembly of the medical device system of FIG. 1, in accordance with implementations.

The tensioning assembly 300 or the weight 405 can include various configurations. For example, as depicted in FIG. 4A, the tensioning assembly 300 can include a plurality of weights 405 connected by one or more connectors 125 or by other means. The weights 405 can be evenly distributed about each of the lines 135 (e.g., each line 135 can connect with at least one weight 405 at a distance from one another) or the weights 405 can be unevenly distributed. The weights 405 can be sized or shaped to easily couple with the lines 135 or with the connectors 125. For example, the weights 405 can include at least one aperture 410 (e.g., hole, slot, opening, etc.) that can at least partially receive a portion of a connector 125 or the line 135 to couple the weight with the connector 125 or line 135. With this configuration, the tensioning assembly 300 can be customizable based on the weight or size of the patient using the medical device system 100.

Figure 4B:
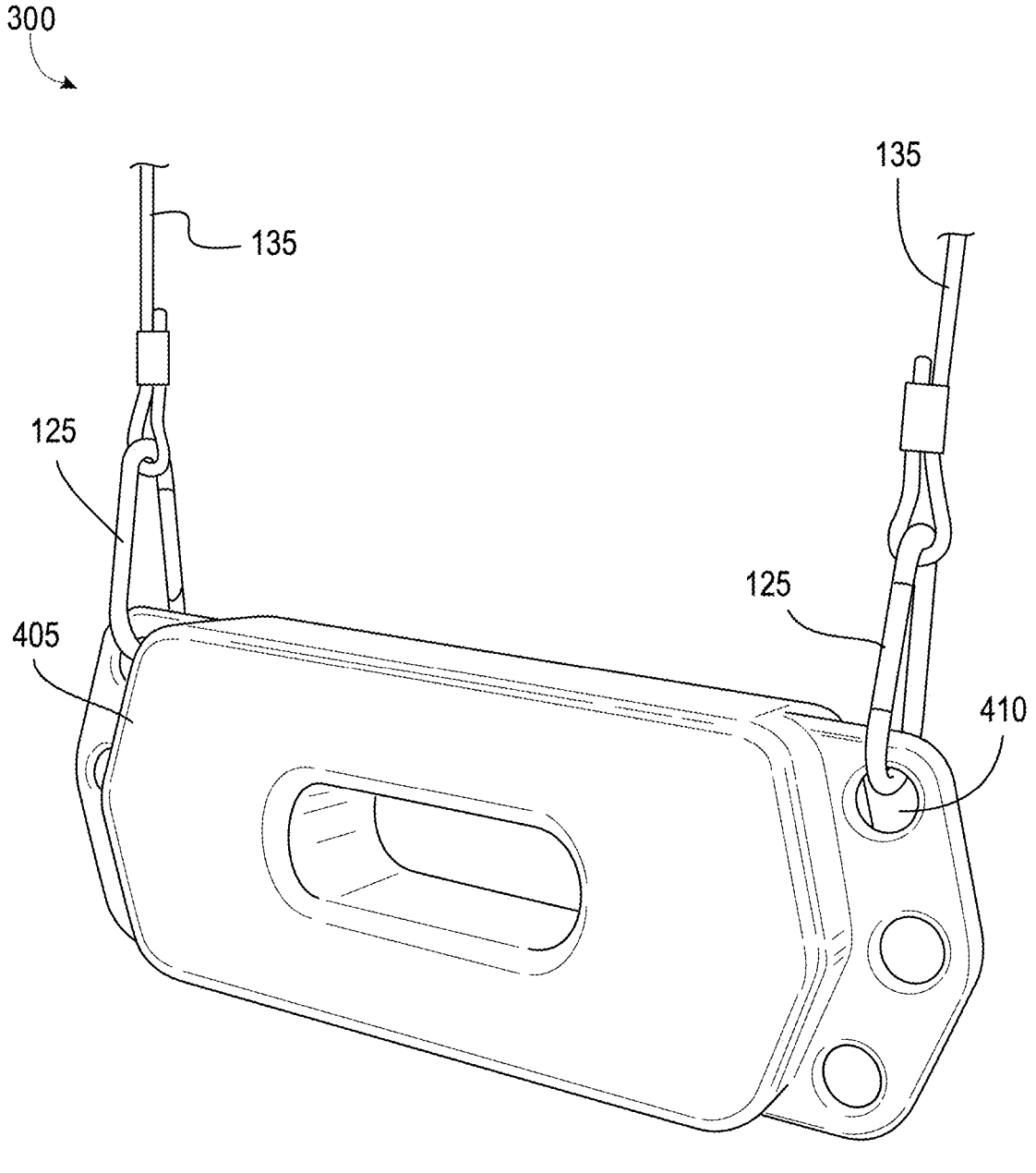
Figure 4C:
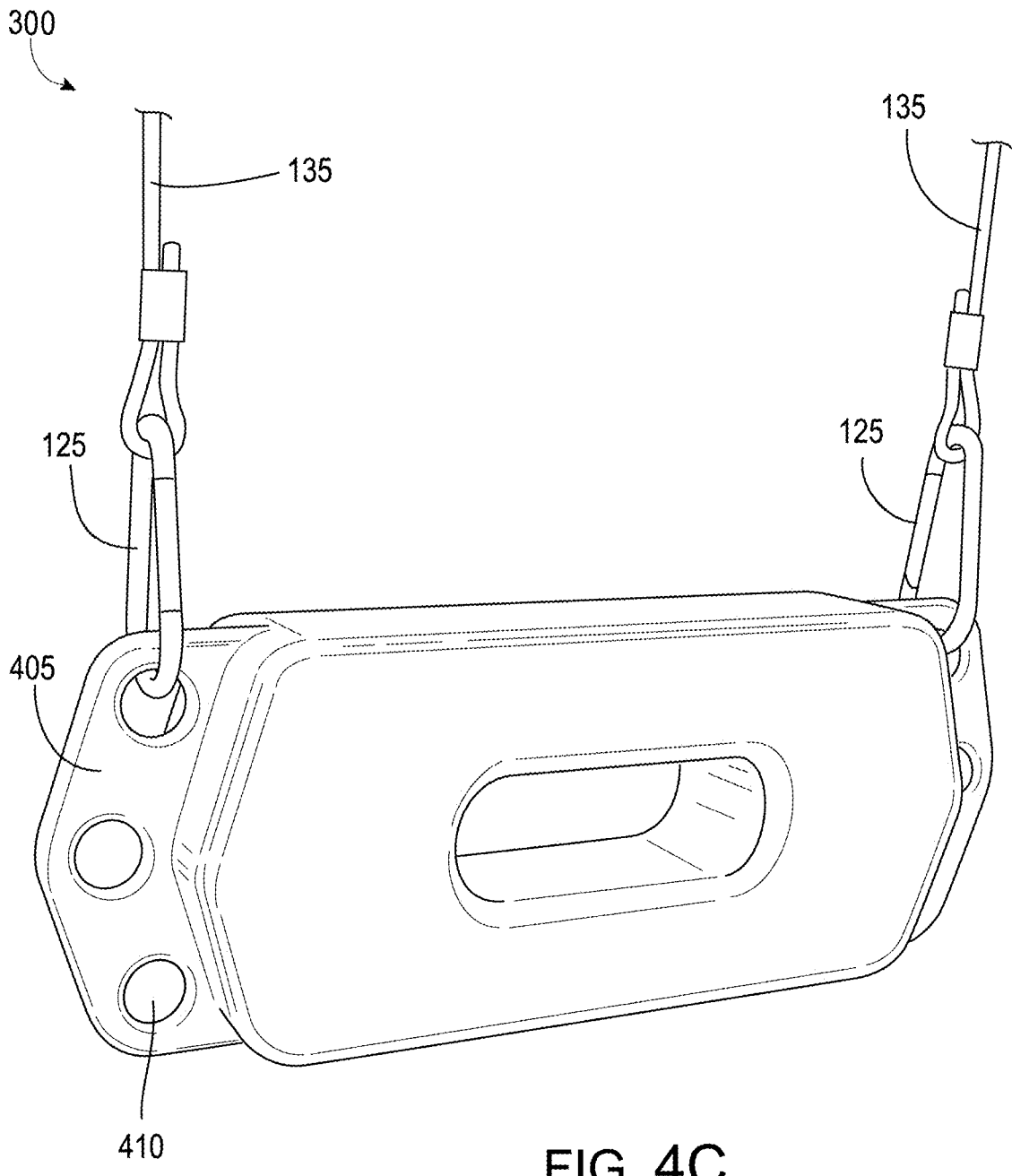

The tensioning assembly 300 can include one weight 405, as depicted in at least FIGS. 4B and 4C. The weight 405 can be evenly distributed about each of the lines 135 (e.g., each line 135 can connect with the weight 405 at a distance from one another) or the weight 405 can be unevenly distributed. The weight 405 can be sized or shaped to easily couple with the lines 135 or with the connectors 125 via the at least one aperture 410 (e.g., hole, slot, opening, etc.) that can at least partially receive a portion of a connector 125 or the line 135 to couple the weight with the connector 125 or line 135.

Figure 4D:
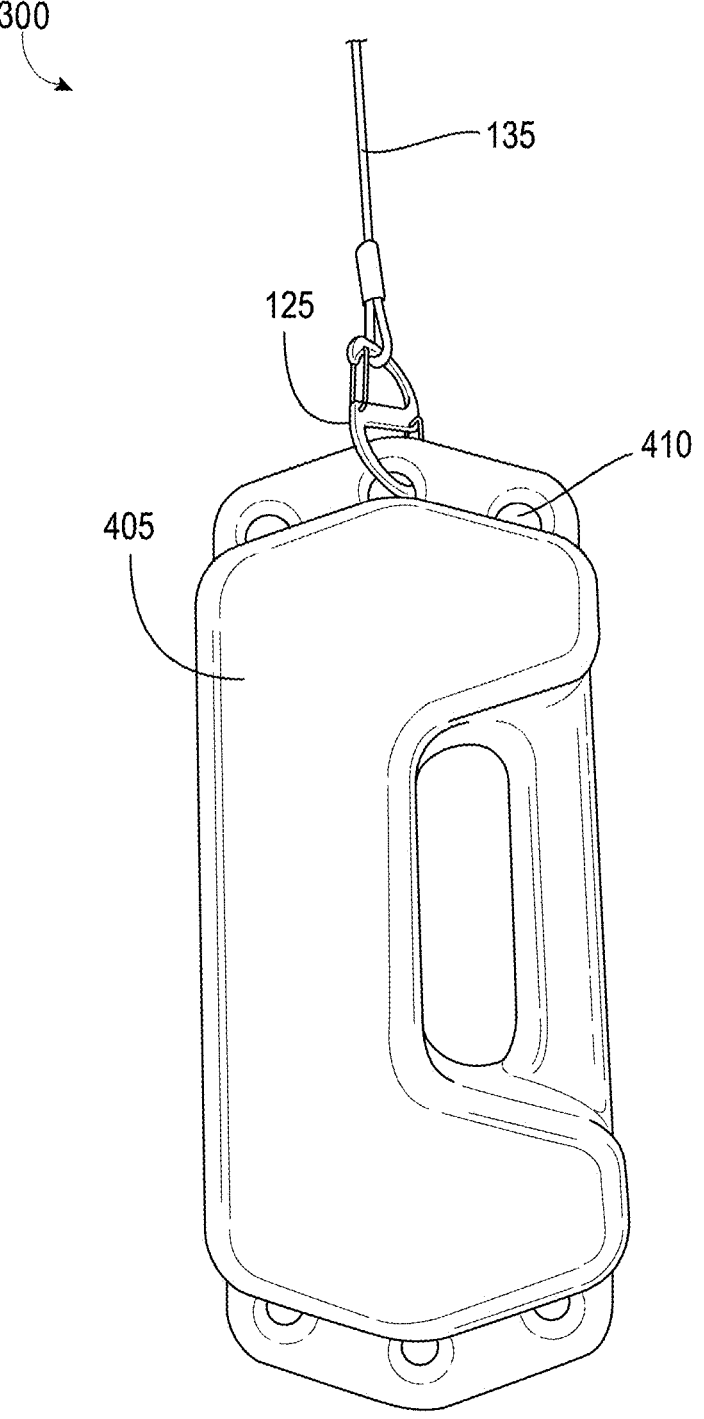
Figure 4E:
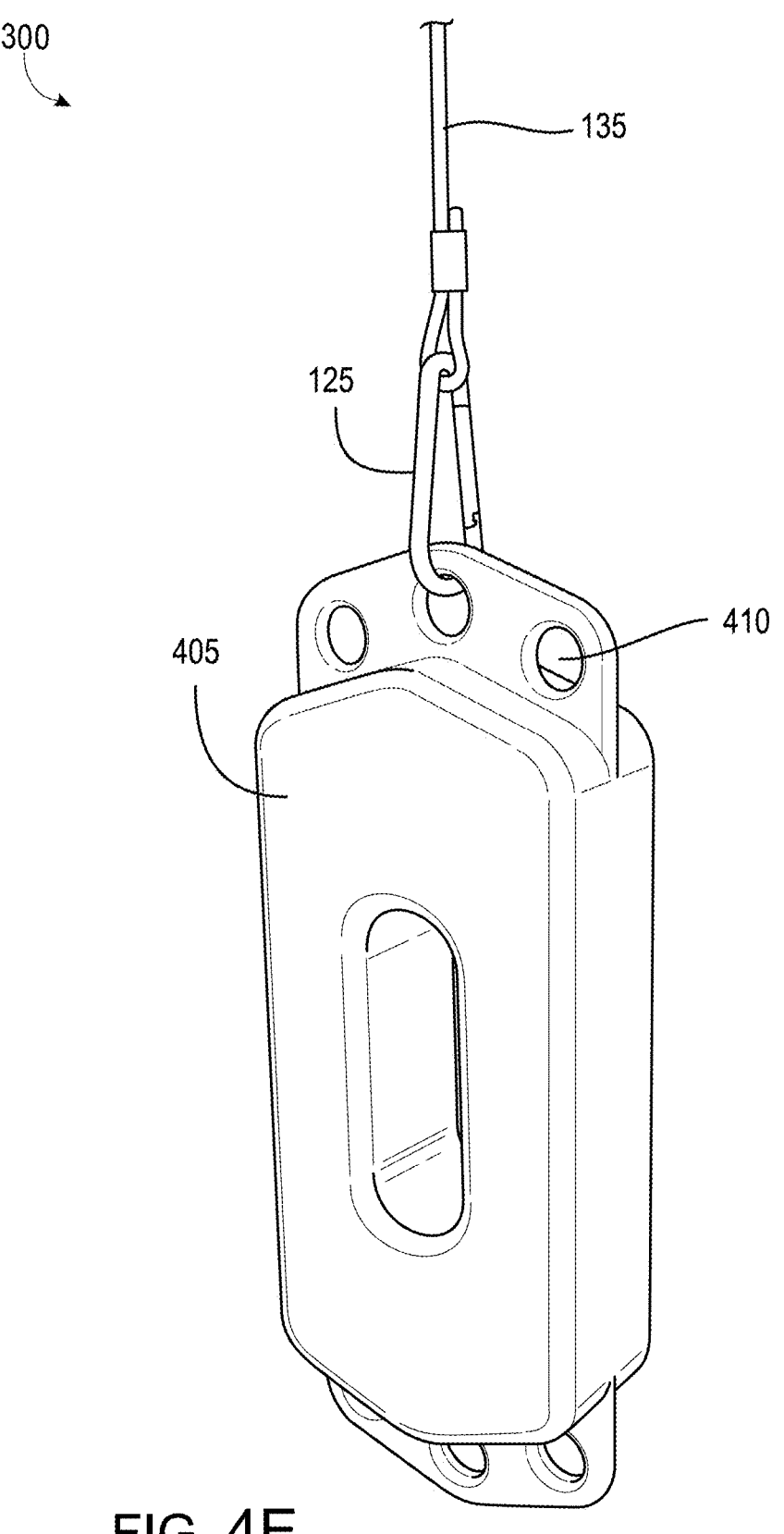

The one or more weights 405 can couple with one line 135 or each line 135 can couple with the weight 405 at the same or approximately the same location, as depicted in at least FIGS. 4D and 4E. For example, each line 135 can couple with a respective weight 405 such that the one or more lines 135 can couple with different weights of the same weight or of a different weight. By way of example, a first line 135 can couple with a first weight 405 of about 15 lbs. via a first connector 125 and a second line 135 can couple with a second weight 405 of about 15 lbs. or less than or greater than 15 lbs. via a second connector 125. This example is illustrative, the weights can be significantly greater or lesser than 15 lbs. (e.g., 0.5 lb. to 100 lbs. or another range or weight). With this configuration, the force applied to different sides of the medical device system 100 can vary. The weight 405 can be sized or shaped to easily couple with the one or more lines 135 or with the connectors 125 via the at least one aperture 410 (e.g., hole, slot, opening, etc.) that can at least partially receive a portion of a connector 125 or the line 135 to couple the weight with the connector 125 or line 135.

Figure 4F:
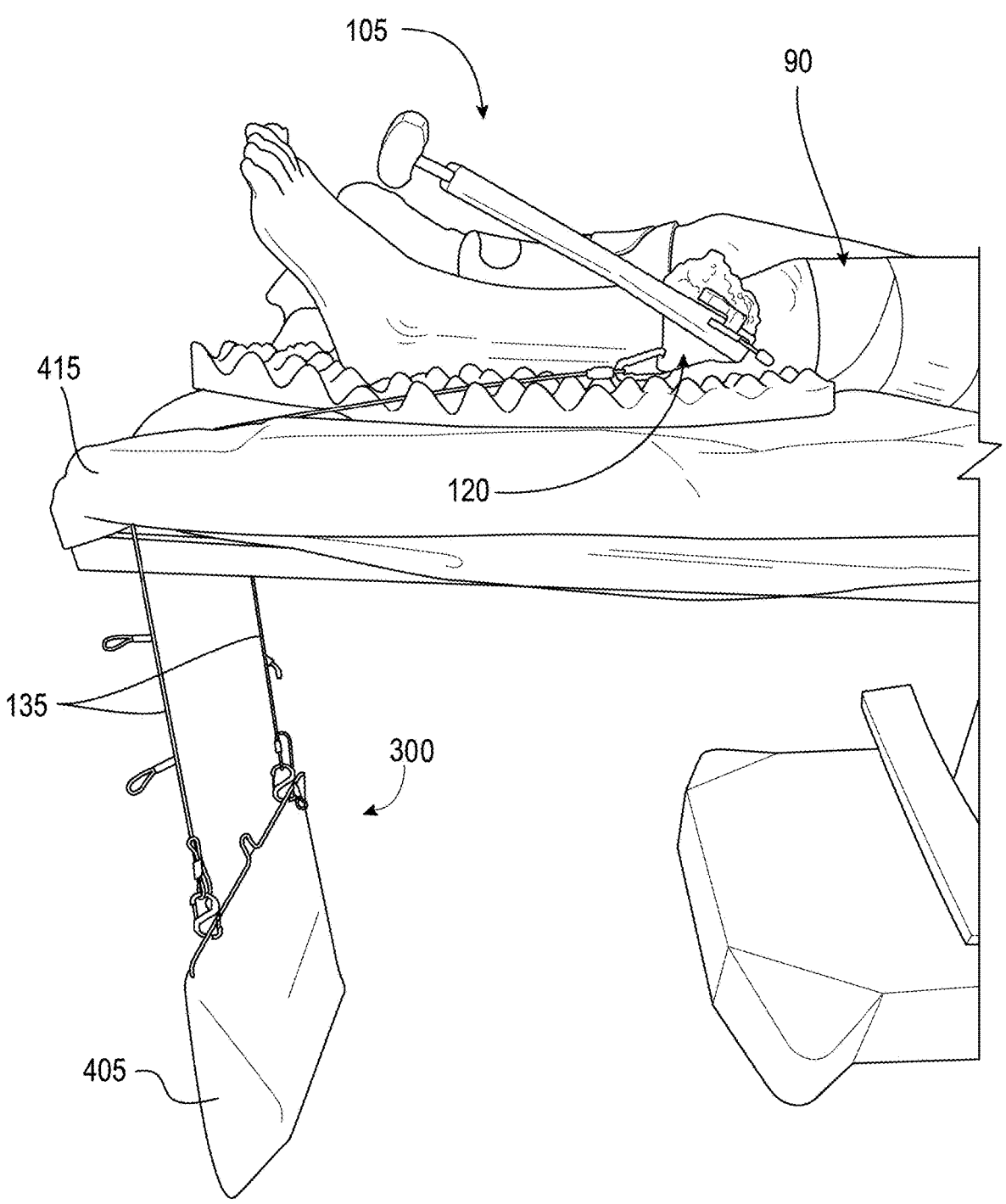
Figure 4G:
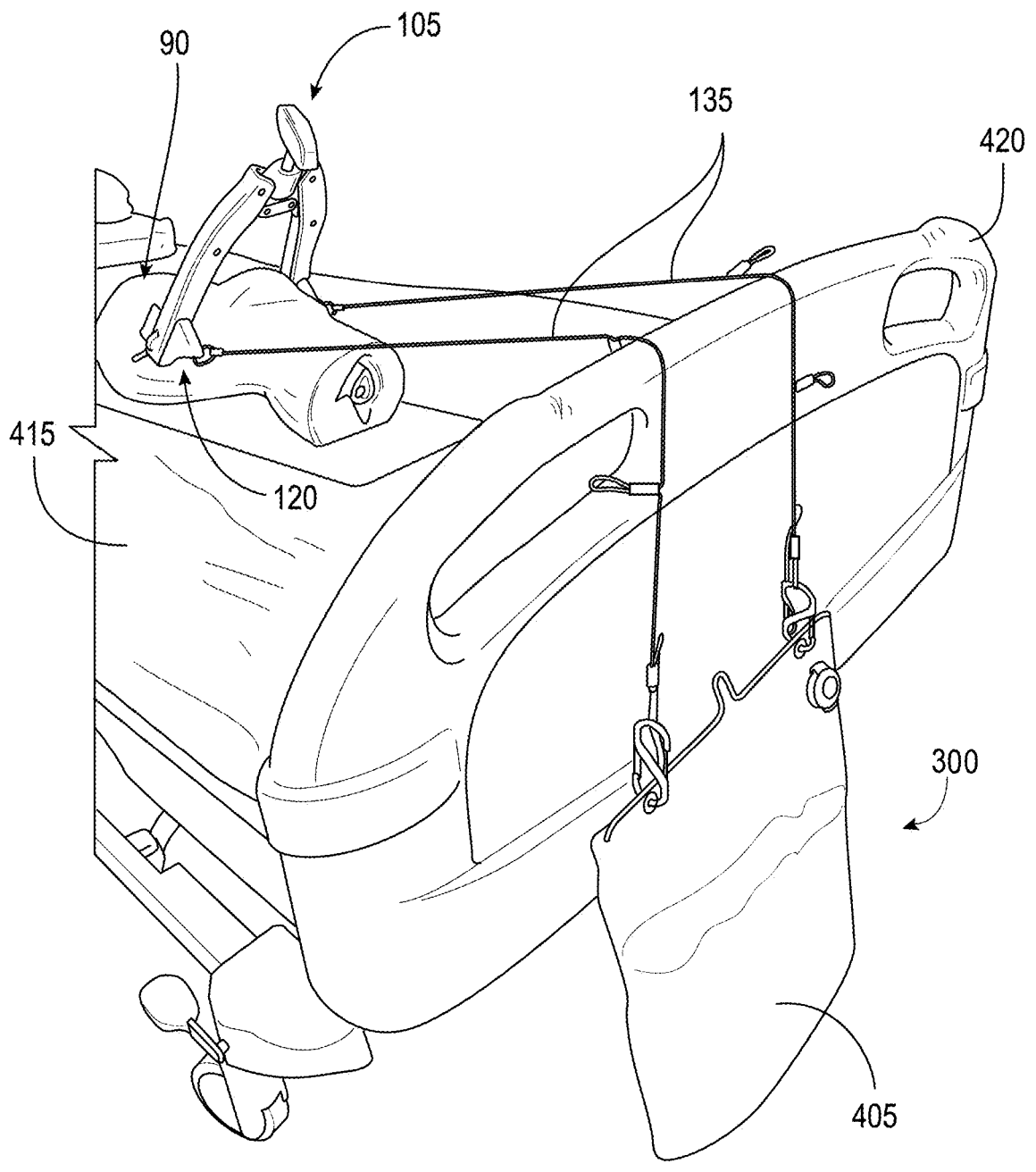

The one or more weights 405 can be or can include a fluid bag, as depicted in FIGS. 4F and 4G. For example, the weight 405 can include a bag that can be filled to a specific volume of fluid (e.g., water or another fluid) to customize the weight 405. This configuration can allow the medical device system 100 to be fully single use since the weight 405 (e.g., the bag) can be disposed of after use or reused again for another patient of the same height and weight or of another height and weight.

The one or more weights 405 (e.g., pre-made weights or fluid bags) can be positioned at various heights or locations relative to the user based on a desired force. For example, as depicted in FIG. 4F, the lines 135 can be positioned such that the lines 135 contact an end of a bed 415 (e.g., hospital bed) or other surface where the patient 90 is located and extend at an approximately 90 degree angle relative to the bed 415 to couple with the one or more weights 405. With reference to FIG. 4G, among others, the lines 135 can be positioned such that the lines 135 do not contact or at least partially avoid contacting the bed 415 or other surface where a patient 90 is located. For example, the lines 135 can be positioned at or over an end 420 of a bed 415 or other surface where the patient 90 is located and can extend at an angle to couple with the weight 405. In this manner, the positioning of the one or more weights 405 can be adjustable.

Responsive to a force (e.g., a substantially horizontal force) applied to the tensioning assembly 300 (e.g., by a user pulling the bar 115, by a weight 405 applied to the bar 115, or via another force), the adapter 120 can facilitate causing a portion of the medical device 105 to pivot from a first position, in which the medical device 105 is at least partially contacting or applying a force to an external portion of the patient 90 (e.g., to the knee or leg of the patient 90, skin of the patient 90, or other portions of the anatomy of the patient 90) to a second position, in which the medical device 105 is not contacting or applying a force to an external portion of the patient 90. For example, a force applied to the tensioning assembly 300 in a direction substantially parallel with a first position axis 150 (FIG. 1) can cause a body of the medical device 105 to pivot, by the adapter 120, such that the body of the medical device 105 moves from being substantially parallel with the first position axis 150 to being substantially parallel with a second position axis 154 (e.g., the longitudinal axis of the medical device 105 at the second position between a first end of the body and a second end of the body as depicted in at least FIG. 1). In other words, the adapter 120 can facilitate pivoting a body of the medical device 105 an angle 152 in the range of 15-165 degrees (e.g., 15-45 degrees, 15-30 degrees, 20-25 degrees, or in another range) relative to a portion of the patient 90 (e.g., relative to an approximate axis extending through, for example, a patient's leg as depicted in FIG. 1) when a force is applied to the adapter 120 via, for example, the line 135 and the tensioning assembly 300 (e.g., the weights 405 or force applied by a user).

Figure 5:
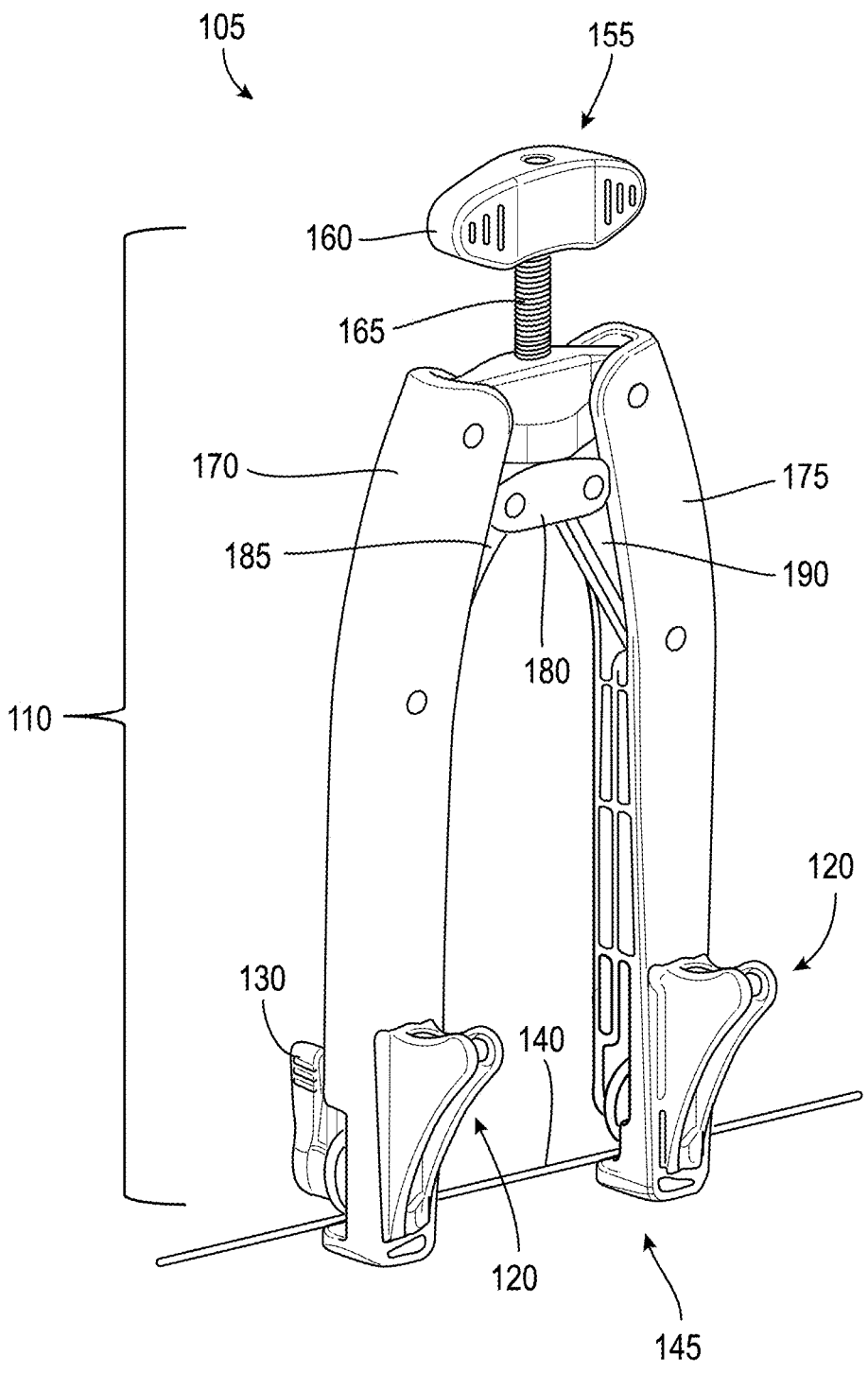
FIG. 5 is an example perspective view of a medical device of the medical device system of FIG. 1, in accordance with implementations.
Figure 6:
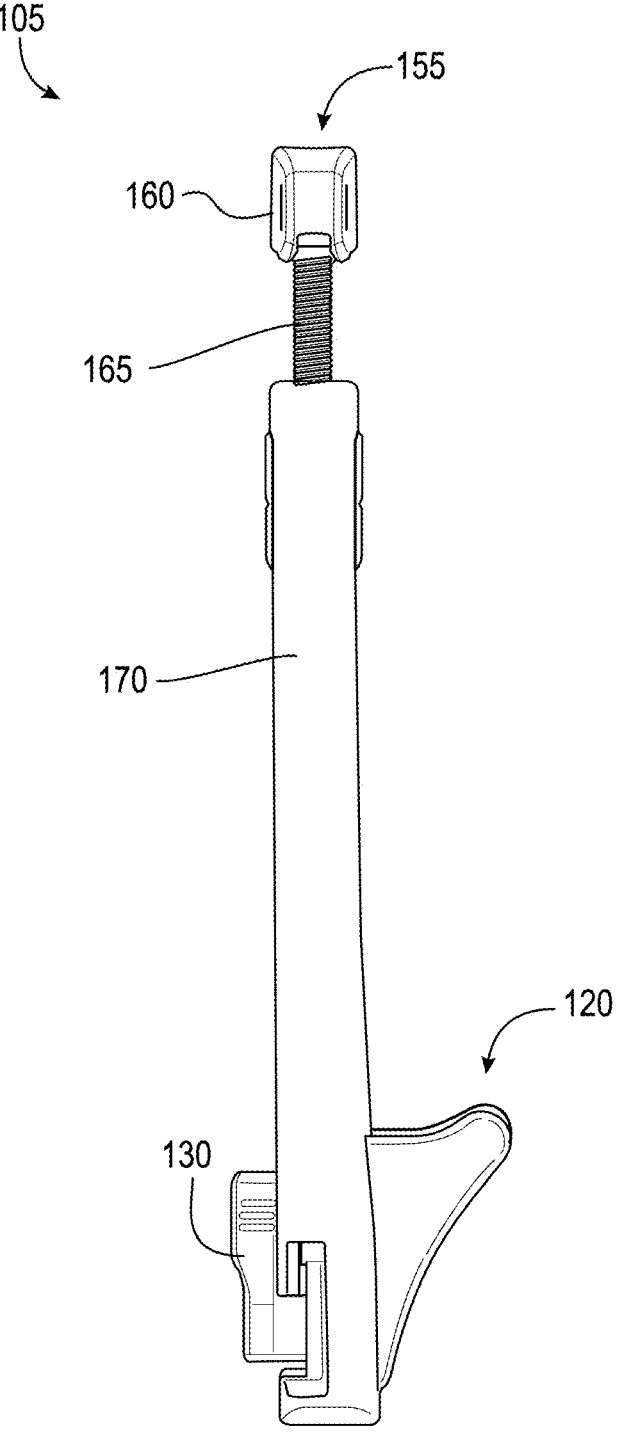
FIG. 6 is an example side view of the medical device of FIG. 5, in accordance with implementations.
Figure 7:
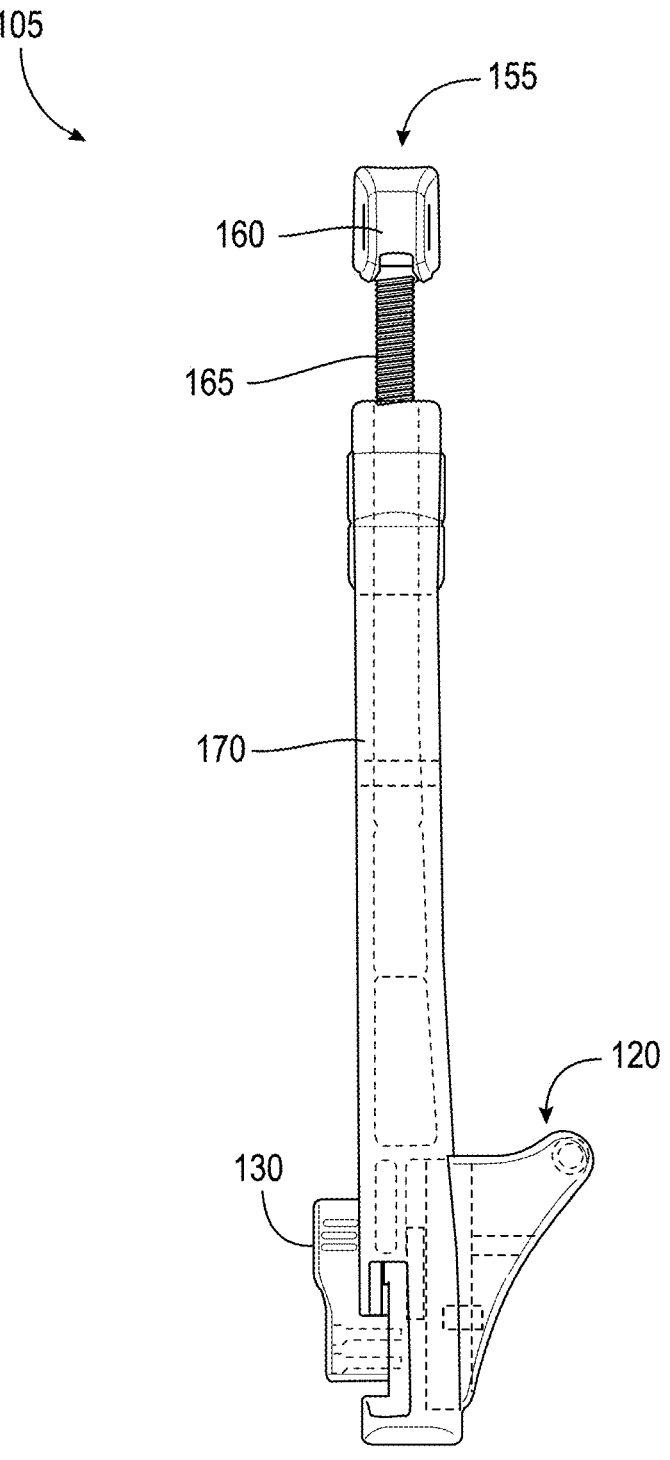
FIG. 7 is an example side view of the medical device of FIG. 5 in which a portion of the medical device is transparent, in accordance with implementations.
Figure 8:
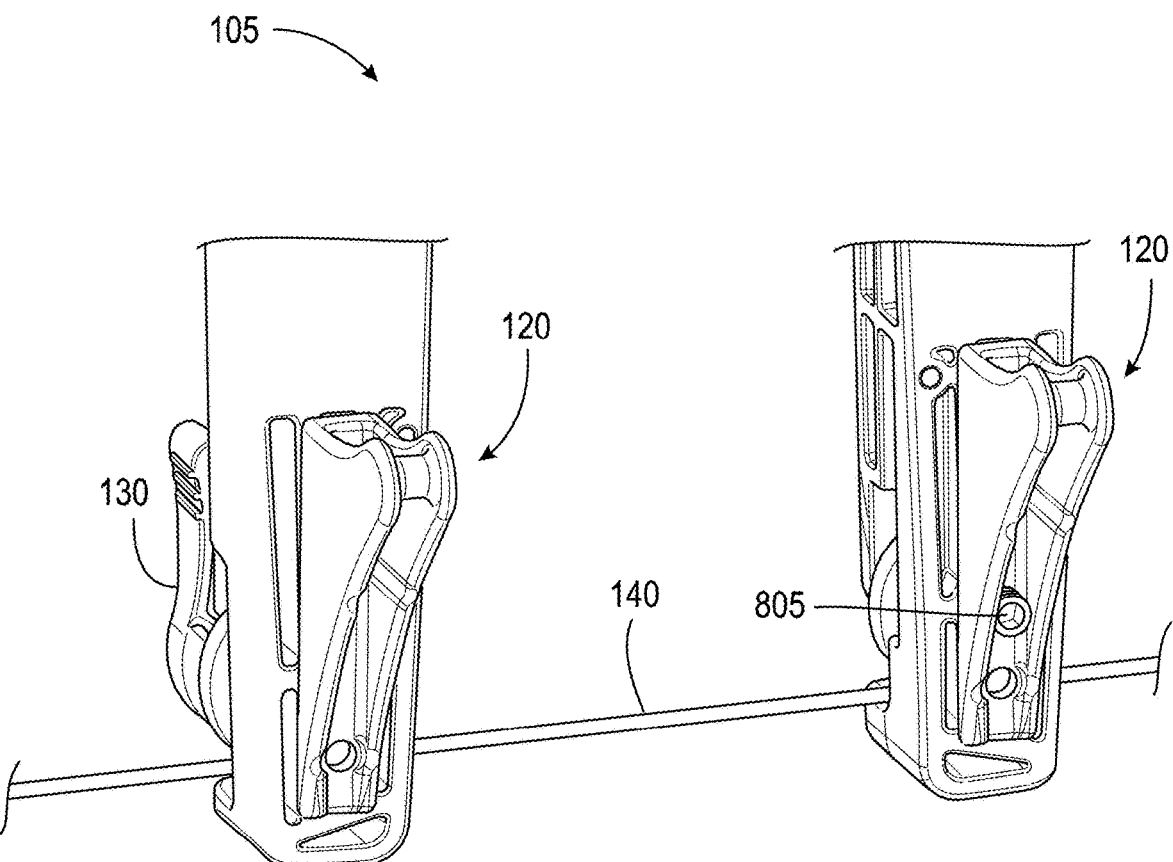
FIG. 8 is an example detailed perspective view of a portion of the medical device of FIG. 5, in accordance with implementations.

FIG. 5 depicts an example perspective view of the medical device 105, FIG. 6 depicts an example side view of the medical device 105, FIG. 7 depicts an example side view of the medical device 105 with a portion of the medical device 105 being transparent, and FIG. 8 depicts an example detailed perspective view of a portion of the medical device 105.

The medical device 105 can include a body 110 having a first end 145 and a second end 155. The first end 145 can oppose the second end 155. The first end 145 can be positioned in other various positions relative to the second end 155 (e.g., adjacent to). The body 110 can include a first extension 170 that extends between the first end 145 and the second end 155. The body 110 can include a second extension 175 that extends between the first end 145 and the second end 155. The first extension 170 can oppose the second extension 175. The first extension 170 or the second extension 175 can extend substantially parallel (e.g., within 10 degrees) with a longitudinal axis of the body 110 of the medical device 105. For example, as depicted in at least FIG. 1, the first extension 170 or the second extension 175 can extend substantially parallel with the second position axis 154 (i.e., the first extension 170 and the second extension 175 run parallel to one another). The first extension 170 can adjustably couple with the second extension 175 by one or more adjusting members. For example, the first extension 170 and the second extension 175 can adjustably couple with one another by a linkage mechanism (e.g., a first linkage 180, a second linkage 185, and a third linkage 190). Movement of the linkage mechanism can cause the first extension 170 and the second extension 175 to move away from one another or towards one another.

The first end 145 can include at least one locking cam 130. For example, the first end 145 can include two spring-loaded locking cams 130. The spring-loaded locking cams 130 can be or can include one or more nuts, screws, clamps (e.g., toggle clamps), cam mechanisms (e.g., wedge cams), ratchets, clamping levers, sliding mechanisms, or other components that can facilitate fixing a pin 140 relative to the body 110 of the medical device 105. For example, the cam 130 can be or can include one or more slots, grooves, holes, or other openings that can at least partially receive the pin 140. The pin 140 can be or can include a device, apparatus, component, or fixture that couples with or engages with one or more of a muscle, bone, tendon, or ligament of a patient. For example, the pin 140 can be a pin or wire that can penetrate through a portion of a femur bone (e.g., a 2 mm. stainless steel pin or another pin, such as a pin having a diameter in the range of 1-4 mm.).

The body 110 can include at least one handle 160. The handle 160 can rigidly couple with a fastener 165 such that turning the handle 160 in one direction causes the fastener 165 to turn in the direction. For example, the fastener 165 can operably couple with at least a portion of the linkage mechanism of the body 110 such that movement of the fastener 165 (by the handle 160) can cause the linkage mechanism to move and therefore cause the extensions 170, 175 to move.

As described herein, each extension 170, 175 of the body 110 can include an adapter 120. For example, the first extension 170 can include a first adapter 120 and the second extension 175 can include a second adapter 120. As depicted throughout the figures, the adapter 120 can include a substantially triangular shape in which a first portion of the adapter 120 (e.g., a portion positioned adjacent or contacting an extension 170, 175) couples with a corresponding extension 170, 175 and a second portion of the adapter 120 (e.g., a portion positioned opposite the extension 170, 175) can couple with a portion of the tensioning assembly. The adapter 120 can protrude outward at an angle from a surface of the corresponding extension 170, 175 (e.g., in a substantially triangular shape). The adapter 120 can include various other shapes including, but not limited to, circular, square, rectangular, asymmetrical, or various other shapes. The adapters 120 can be made from various materials including, but not limited to, plastic or metal.

Figure 9:
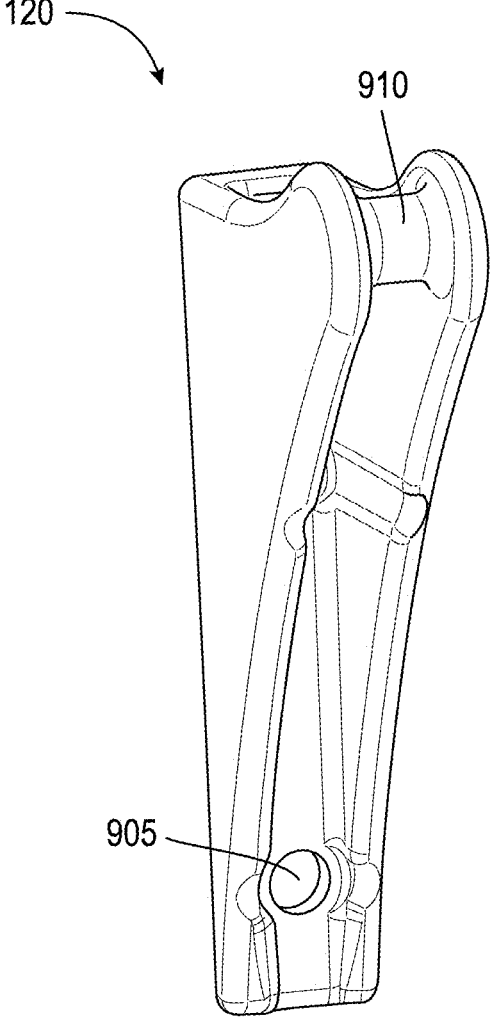
FIG. 9 is an example rear perspective view of an adapter of the medical device of FIG. 5, in accordance with implementations.
Figure 10:
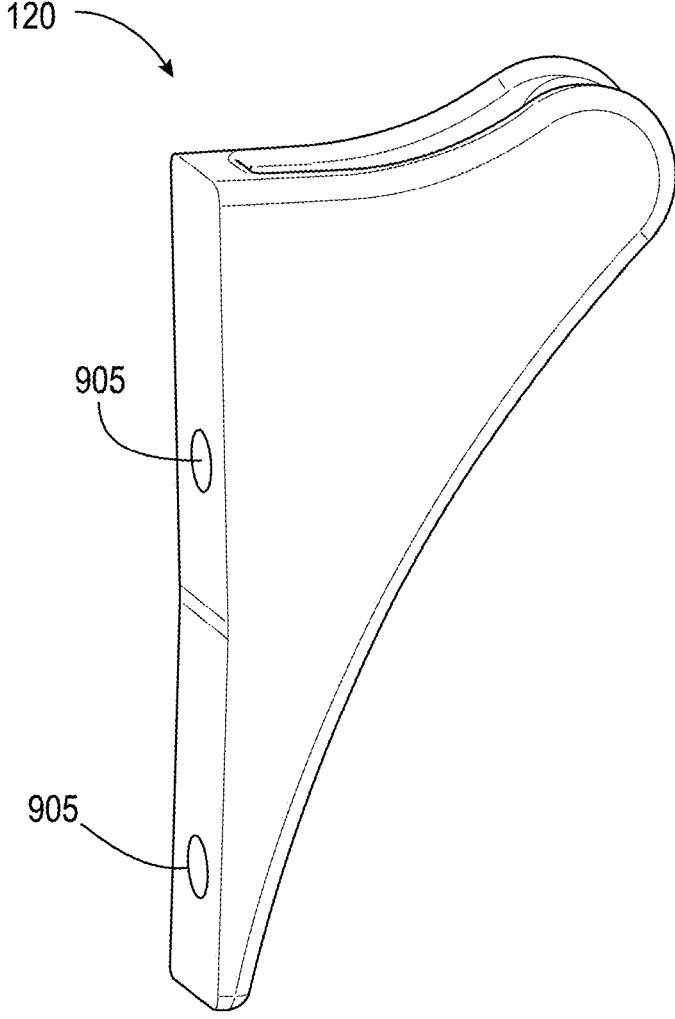
FIG. 10 is an example front perspective view of the adapter of FIG. 9, in accordance with implementations.

FIG. 9 depicts a rear perspective view of an adapter 120 and FIG. 10 depicts a front perspective view of the adapter 120, according to an example. The adapters 120 can couple with a corresponding extension 170, 175 in various ways. For example, as depicted in at least FIG. 8, the adapter 120 can couple with the corresponding extension 170, 175 by at least one fastener 805. For example, the adapter 120 can include at least one partially hollow portion having at least one hole 905 (e.g., opening or aperture) to receive the fastener 805. The fastener 805 can extend through a portion of the corresponding extension 170, 175 to fix the adapter 120 with the extension 170, 175. For example, the first extension 170 or the second extension 175 can include at least one threaded hole corresponding to the hole 905 of the adapter 120 to receive a fastener 805. The threaded holes of the extensions 170, 175 can be molded into a portion of the extension 170, 175 during manufacturing. The adapter 120 can include multiple holes 905 that can each receive a fastener 805. The adapter 120 can couple with the corresponding extension 170, 175 in various additional or alternative ways including, but not limited to, via clamps, adhesives, welded joints, or other ways. The adapter 120 can be monolithically formed with a portion of the corresponding extension 170, 175 (e.g., such that the extension and the adapter 120 are formed simultaneously during manufacturing).

The adapter 120 can couple with a portion of the tensioning assembly 300 in various ways. For example, the adapter 120 can include at least one connecting member 910 that can couple with at least one connector 125 or at least one line 135 of the tensioning assembly 300. For example, the connecting member 910 can include one or more of an opening (e.g., hole), slot, rod, or other component. For example, as depicted in FIG. 9, the connecting member 910 can include a rod that extends between a first portion of the adapter 120 and a second portion of the adapter 120. The rod can be at least partially surrounded by a hollow space (e.g., slot to receive a portion of the tensioning assembly) such that a line 135 or a connector 125 can extend around the rod to couple with the rod, as depicted in at least FIG. 1. The adapter 120 can couple with the line 135, connector 125, or other portion of the tensioning assembly 300 in various additional or alternative ways including, but not limited to, through fasteners, clamps, knots, welding, or various other means.

Figure 11:
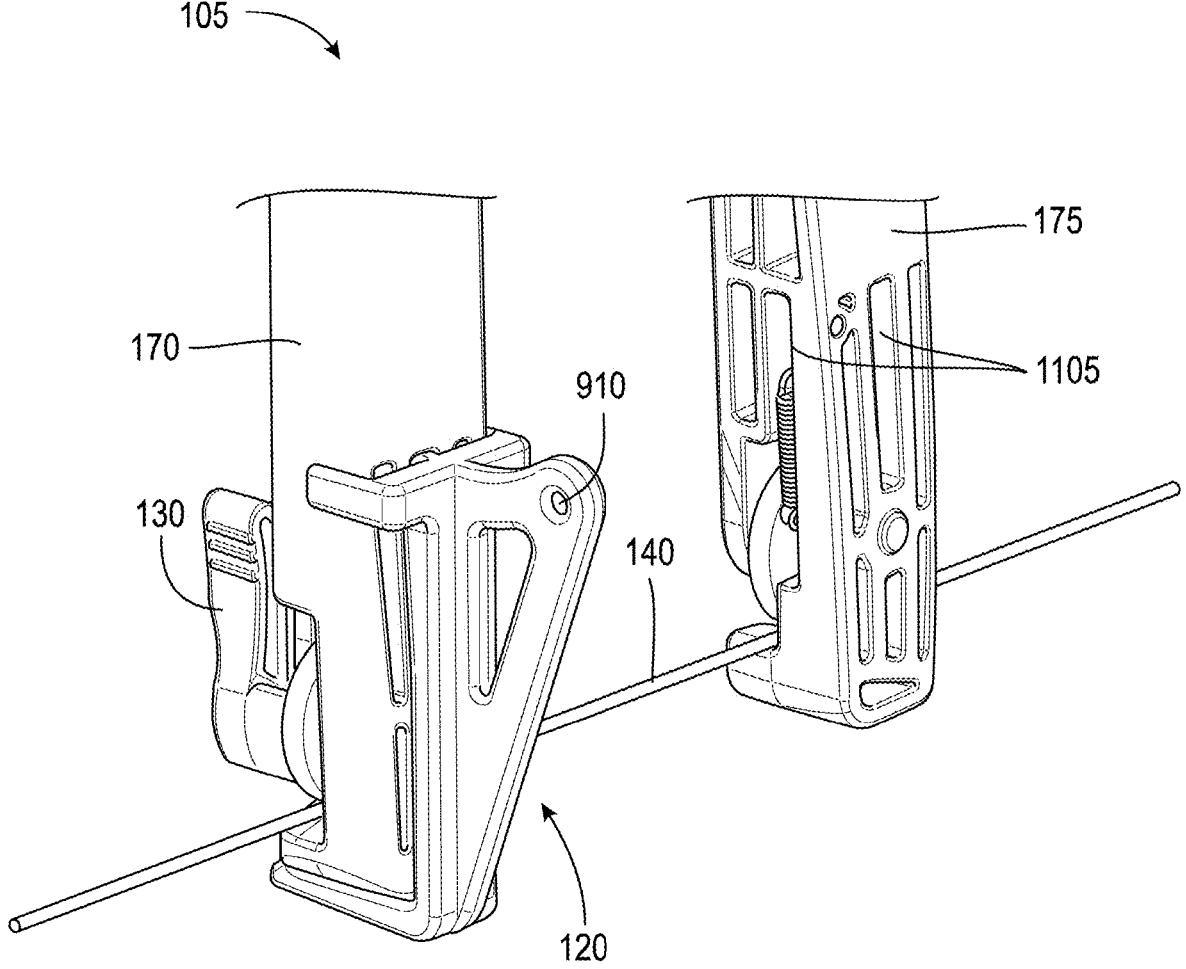
FIG. 11 is another example detailed perspective view of a portion of the medical device of FIG. 5, in accordance with implementations.
Figure 12:
FIG. 12 is an example rear perspective view of an adapter of the medical device of FIG. 5, in accordance with implementations.
Figure 12:
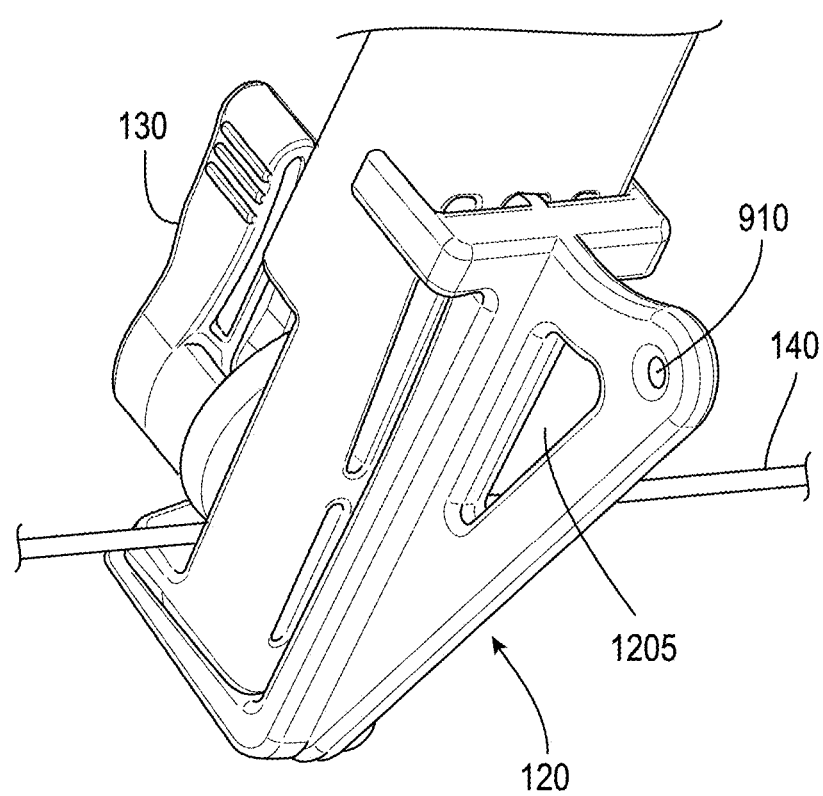
Figure 13:
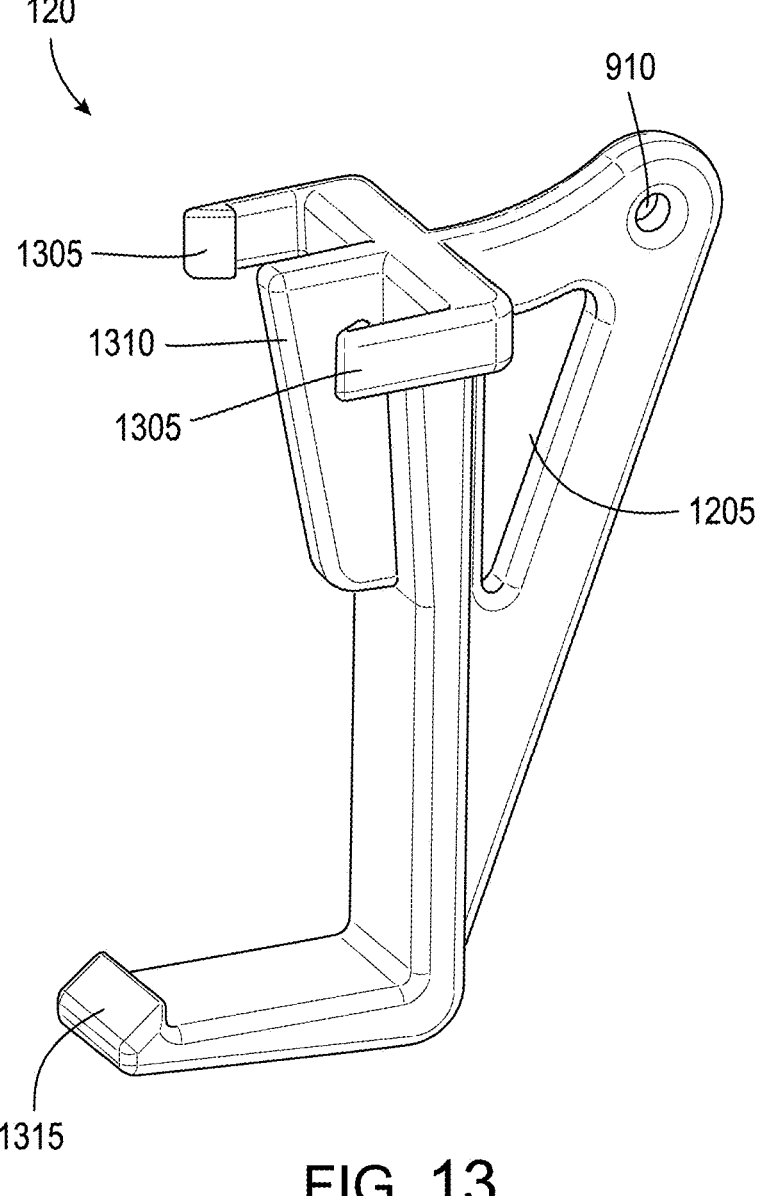
FIG. 13 is an example front perspective view of the adapter of FIG. 12, in accordance with implementations.

FIG. 11 depicts another perspective view of a portion of the medical device 105 and FIG. 12 depicts a perspective detailed view of a portion of the medical device 105, according to an example. FIG. 13 depicts an example perspective view of an adapter 120 of the medical device 105, according to an example. As depicted in at least FIGS. 11-13, the one or more adapters 120 can include at least one protrusion 1310. For example, the adapter 120 can include a protrusion 1310 that can extend from a surface of the adapter 120 to extend through and couple with a slot 1105 (e.g., an at least partial opening to receive the protrusion 1310) of the corresponding extension 170, 175. The adapter 120 can include at least one tab 1305, 1315. For example, the adapter 120 can include two outer tabs 1305 that protrude from the adapter 120 and extend at least partially along a side portion of the corresponding first extension 170 or the second extension 175. For example, at least one tab 1305 can include a snap fit feature that facilitates snapping into or onto a portion of the corresponding extension 170, 175. The extension 170, 175 can include at least one slot 1105 (e.g., an at least partial opening to receive a tab 1305) positioned along a side of the extension 170, 175 to receive a portion of the tab 1305, for example.

The adapter 120 can include an end tab 1315 having at least one snap fit feature to snap onto a portion of an end of the corresponding extension 170, 175 (e.g., an end positioned at the first end 145 of the medical device 105), as depicted in at least FIG. 11. The protrusion 1310 extending into a slot 1105 of the corresponding extension 170, 175, the tabs 1305 snap fitting into at least one slot 1105 of the corresponding extension 170, 175, and the end tab 1315 snap fitting onto an end of the corresponding extension 170, 175 can facilitate locking the adapter 120 relative to the corresponding extension 170, 175. The adapter 120 can include at least one cutout 1205 (e.g., in the triangular shape of the adapter 120) to reduce the mass of the adapter 120 or to create an aesthetic effect.

Figure 14:
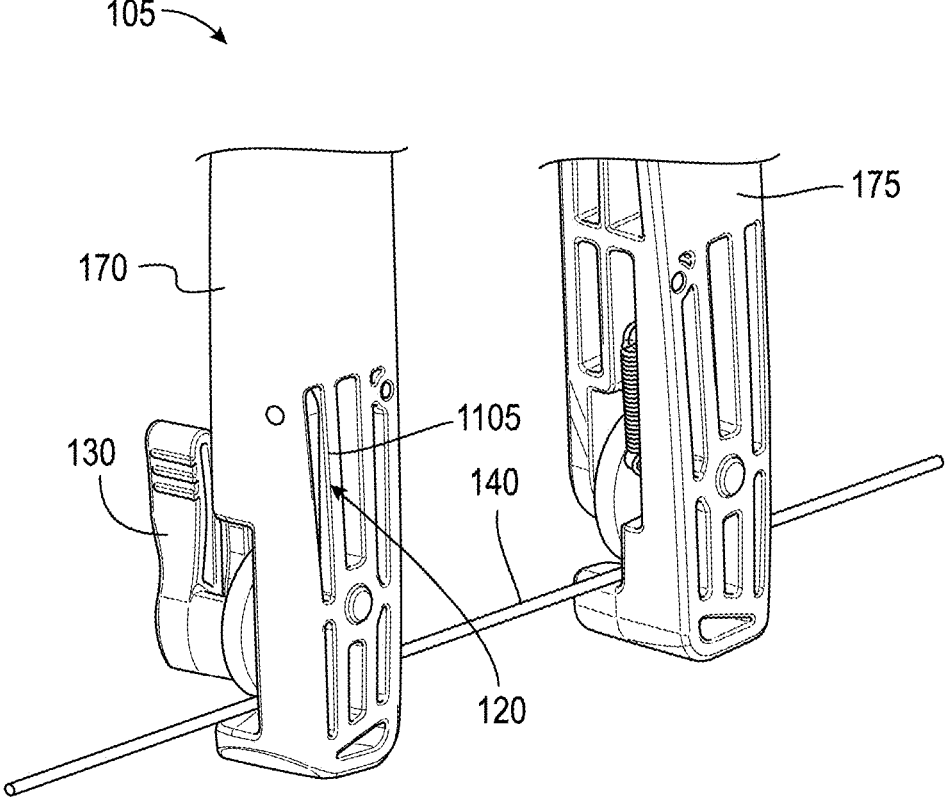
FIG. 14 is an example detailed perspective view of a portion of the medical device of FIG. 5 in a first state, in accordance with implementations.
Figure 15:
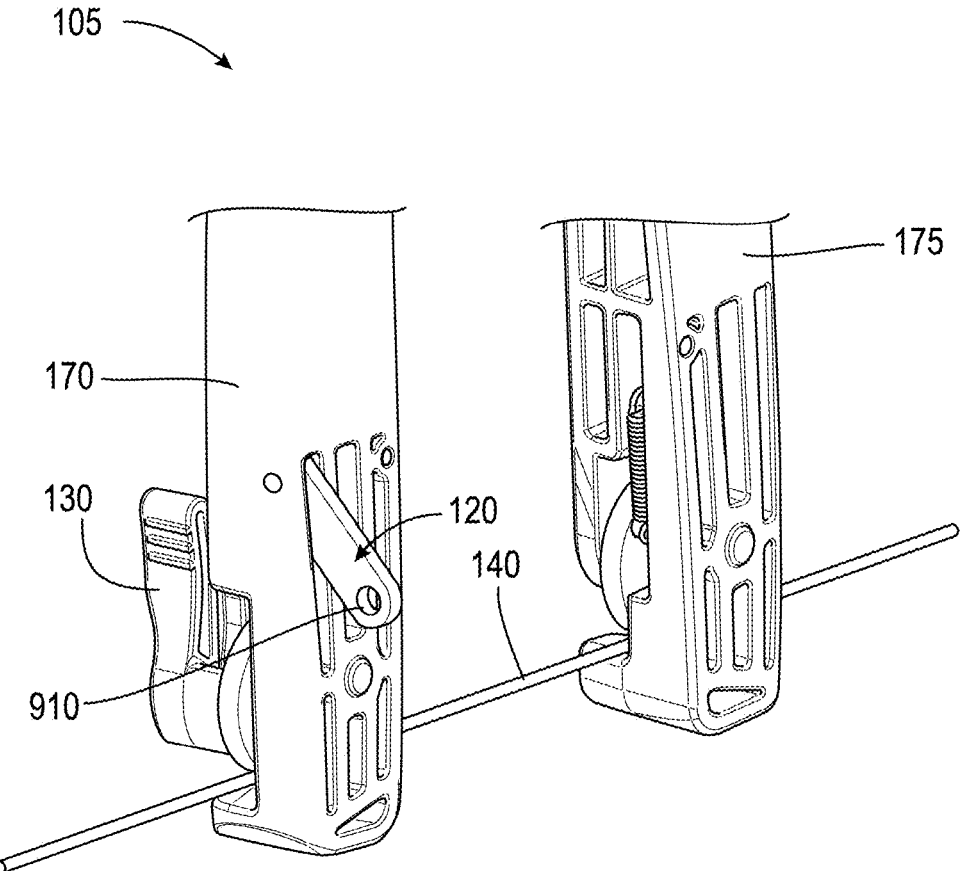
FIG. 15 is an example detailed perspective view of a portion of the medical device of FIG. 5 in a second state, in accordance with implementations.
Figure 16:
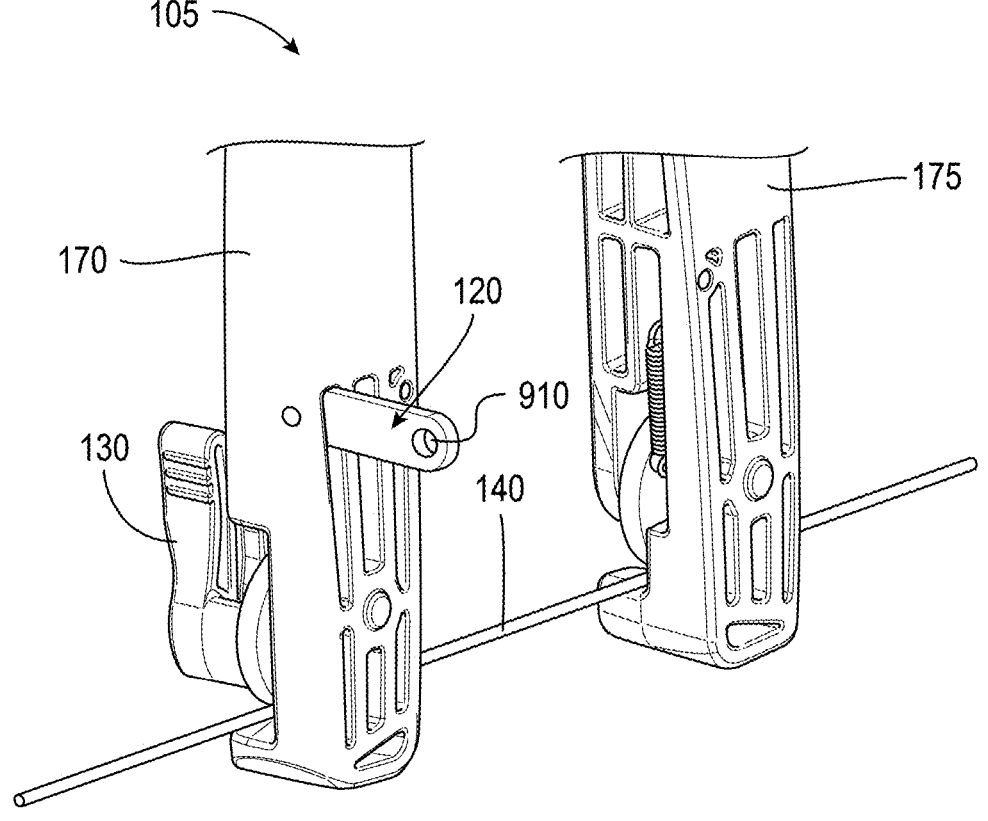
FIG. 16 is an example detailed perspective view of a portion of the medical device of FIG. 5 in a third state, in accordance with implementations.
Figure 17:
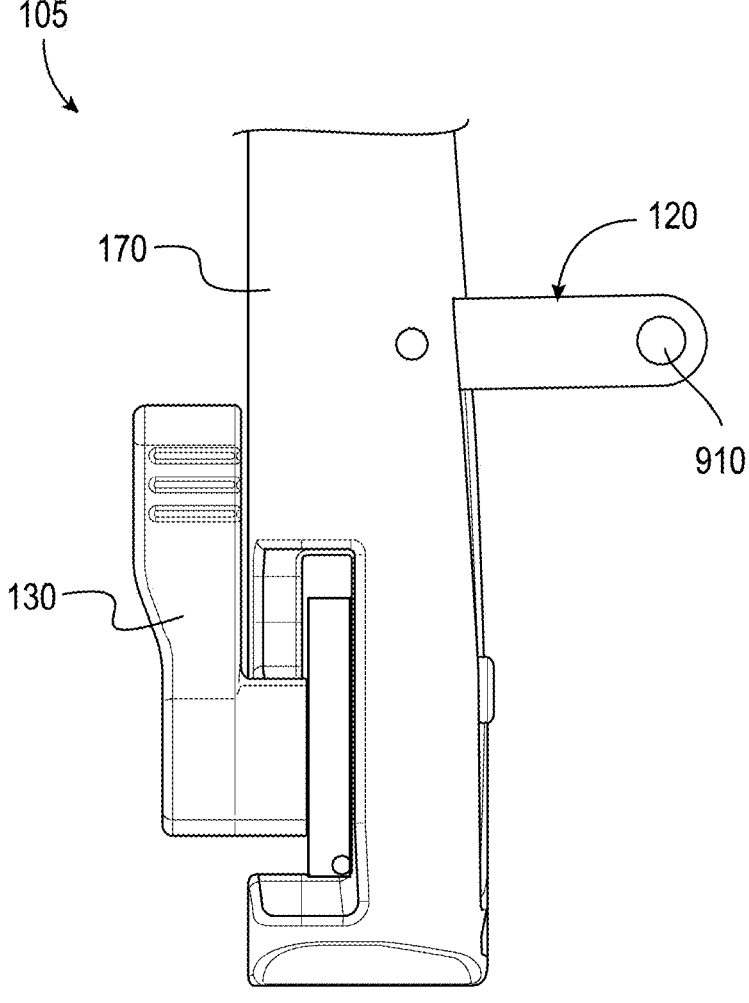
FIG. 17 is a detailed side view of a portion of the medical device of FIG. 5 in the third state, in accordance with implementations.

FIG. 14 depicts another example perspective view of a portion of the medical device 105, according to an example. The medical device 105 can include at least a portion, or an entirety, of the adapter 120 monolithically formed with or recessed into a portion of the corresponding extension 170, 175. For example, the adapter 120 can be recessed into a portion of a slot 1105 of the corresponding extension 170, 175. The adapter 120 can be positioned such that the adapter 120 can extend from the corresponding extension 170, 175 to couple with a portion of the tensioning assembly 300. For example, FIG. 14 depicts the medical device 105 in a first position, in which the adapter 120 is entirely recessed in the first extension 170, FIG. 15 depicts the medical device 105 in a second position, in which the adapter 120 is partially extending out of the first extension 170, and FIGS. 16 and 17 depict the medical device 105 in a third position, in which the adapter 120 is fully extended out of the first extension 170. The adapter 120 can extend from the first extension 170 in various ways. For example, the adapter 120 can extend from the first extension 170 responsive to a force applied to the adapter 120 (e.g., a user pulling the adapter 120 out of the first extension 170, gravity pulls the adapter 120, or other forces). The adapter 120 can be biased to the third position. For example, the adapter 120 can be spring loaded within the first extension 170 and the medical device 105 can include at least one locking fixture (e.g., a cover) that at least partially covers the adapter 120 such that, responsive to removing the locking fixture, the adapter 120 biases outward. The adapter 120 can include at least one connecting member 910 (e.g., hole) to receive a portion of the tensioning assembly, such as the line 135 or the connector 125.

In operation, a pin 140 of the medical device 105 can extend through a portion of a bone of the patient 90. The body 110 of the medical device 105 can couple with the pin 140 by the cams 130. The adapters 120 of the medical device 105 can couple with at least a portion of the tensioning assembly 300 in various ways (e.g., via a connector 125, via the line 135, via a pulley system). A force can be applied to at least a portion of the tensioning assembly 300 (e.g., by a user pulling the spreader bar 115, by at least one weight 405, or in other ways). The force can be applied substantially in a direction parallel to the first position axis 150 depicted in FIG. 1. The force can pull the adapter 120 in a direction to cause the first end 145 of the body 110 to move towards the spreader bar 115 or the weight 405. The force on the adapter 120 facilitates causing the body 110 to pivot from a first position, in which the body 110 or the one or more lines 135 can be resting on a portion of the patient 90 (e.g., on a patient's leg or foot) to a second position, in which the body 110 is no longer contacting the portion of the patient 90. As described herein, the body 110 can pivot an angle 152 in approximately the range of 15-45 degrees. The medical device 105 is easy to manufacture, at least partially disposable, and operable with a 2 mm. pin 140 or another sized pin 140 (e.g., 1-4 mm. diameter pin). Thus, the medical device 105 provides an easy to use, simple device to reduce pain or damage to the patient 90.

The medical device 105 can include a variety of materials. For example, at least a portion of the medical device 105 (e.g., at least the first extension 170 or the second extension 175) can include one or more injection molded plastic materials. The medical device 105 can include a variety of non-metallic materials including, but not limited to, Nylon, Polyethylene Terephthalate (PET or PETE), High-Density Polyethylene (HDPE), Polyvinyl Chloride (PVC or Vinyl), Low-Density Polyethylene (LDPE), Polypropylene (PP), Polystyrene (PS or Styrofoam), elastomers, or other materials.

The adapter 120 can include a variety of materials. For example, at least a portion of the adapter 120 can include one or more injection molded plastic materials. The medical device 105 can include a variety of non-metallic materials including, but not limited to, Nylon, Polyethylene Terephthalate (PET or PETE), High-Density Polyethylene (HDPE), Polyvinyl Chloride (PVC or Vinyl), Low-Density Polyethylene (LDPE), Polypropylene (PP), Polystyrene (PS or Styrofoam), elastomers, or other materials.

The medical device 105, or at least a portion of the medical device 105, can be disposable. For example, a user can dispose of the medical device 105 after one or more uses. The adapter 120 can be disposable such that multiple adapters 120 can attach and detach from one or more bodies 110 of a medical device 105.

Figure 18:
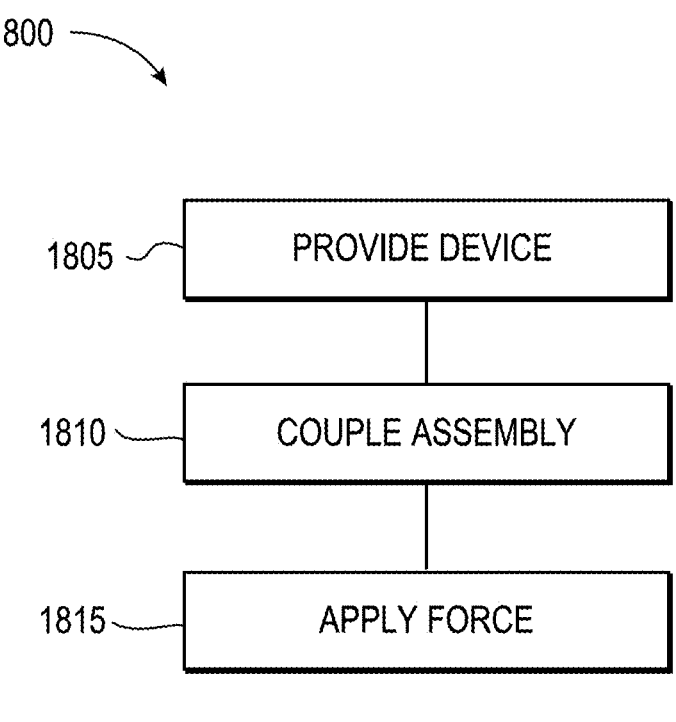
FIG. 18 is an example illustration of a method of using the medical device of the medical device system, in accordance with implementations.

FIG. 18 depicts an example method 1800 of using the medical device 105, according to an example. The method 1800 can include providing the medical device 105, as depicted in act 1805. The medical device 105 can include a body 110 having first end 145 and a second end 155. The first end 145 can oppose the second end 155. The body 110 can include a first extension 170 that extends between the first end 145 and the second end 155. The body 110 can include a second extension 175 that extends between the first end 145 and the second end 155. The first extension 170 can oppose the second extension 175. The first extension 170 or the second extension 175 can extend substantially parallel (e.g., within 10 degrees) with a longitudinal axis of the body 110 of the medical device 105.

Each extension 170, 175 of the body 110 can include an adapter 120. For example, the first extension 170 can include a first adapter 120 and the second extension 175 can include a second adapter 120. The adapter 120 can include a substantially triangular shape in which a first portion of the adapter 120 (e.g., a portion positioned adjacent or contacting an extension 170, 175) couples with a corresponding extension 170, 175 and a second portion of the adapter 120 (e.g., a portion positioned opposite the extension 170, 175) can couple with a portion of the tensioning assembly. The adapter 120 can protrude outward at an angle from a surface of the corresponding extension 170, 175.

The adapters 120 can couple with a corresponding extension 170, 175 in various ways. For example, the adapter 120 can couple with the corresponding extension 170, 175 by at least one fastener 805. The adapter 120 can couple with the corresponding extension 170, 175 by at least one protrusion 1310 or at least one snap fit tab 1305, 1315. The adapter 120 can be monolithically formed or recessed into a portion of the corresponding extension 170, 175 such that the adapter 120 can extend outward from the corresponding extension 170, 175.

The medical device 105 can include at least one pin 140. The pin 140 of the medical device 105 can extend through a portion of a bone of the patient 90. The body 110 of the medical device 105 can couple with the pin 140 by the cams 130.

The method 1800 can include coupling at least a portion of the at least one tensioning assembly 300 with a portion of the one or more adapters 120, as depicted in act 1810. For example, a first adapter 120 coupled with a first extension 170 of the body 110 can couple with a first portion of the tensioning assembly 300 (e.g., with a connector 125, with a line 135, with a spreader bar 115, with a weight 405, or with another portion of the tensioning assembly 300) and a second adapter 120 coupled with a second extension 175 of the body 110 can couple with a second portion of the tensioning assembly 300 (e.g., with a connector 125, with a line 135, with a spreader bar 115, with a weight 405, or with another portion of the tensioning assembly 300).

The method 1800 can include applying a force to the at least one tensioning assembly 300, as depicted in act 1815. For example, a force applied to at least a portion of the tensioning assembly 300 (e.g., by a weight 405, by a user pulling the tensioning assembly 300, by gravity) can cause the body 110 of the medical device to pivot at the adapters 120 to orient the body 110 from a from a first position, in which the body 110 can be resting on a portion of the patient 90 (e.g., on a patient's leg) to a second position, in which the body 110 is no longer contacting the portion of the patient 90.

Figure 19:
FIG. 19 is an example illustration of a method, in accordance with implementations.

FIG. 19 depicts an example method 1900, according to an example. The method 1900 can include providing the medical device 105, as depicted in act 1905. The medical device 105 can include a body 110 having first end 145 and a second end 155. The first end 145 can oppose the second end 155. The body 110 can include a first extension 170 that extends between the first end 145 and the second end 155. The body 110 can include a second extension 175 that extends between the first end 145 and the second end 155. The first extension 170 can oppose the second extension 175. The first extension 170 or the second extension 175 can extend substantially parallel (e.g., within 10 degrees) with a longitudinal axis of the body 110 of the medical device 105. Each extension 170, 175 of the body 110 can include an adapter 120. For example, the first extension 170 can include a first adapter 120 and the second extension 175 can include a second adapter 120. The adapter 120 can include a substantially triangular shape in which a first portion of the adapter 120 (e.g., a portion positioned adjacent or contacting an extension 170, 175) couples with a corresponding extension 170, 175 and a second portion of the adapter 120 (e.g., a portion positioned opposite the extension 170, 175) can couple with a portion of the tensioning assembly. The adapter 120 can protrude outward at an angle from a surface of the corresponding extension 170, 175.

The adapters 120 can couple with a corresponding extension 170, 175 in various ways. For example, the adapter 120 can couple with the corresponding extension 170, 175 by at least one fastener 805. The adapter 120 can couple with the corresponding extension 170, 175 by at least one protrusion 1310 or at least one snap fit tab 1305, 1315. The adapter 120 can be monolithically formed or recessed into a portion of the corresponding extension 170, 175 such that the adapter 120 can extend outward from the corresponding extension 170, 175.

The medical device 105 can include at least one pin 140. The pin 140 of the medical device 105 can extend through a portion of a bone of the patient 90. The body 110 of the medical device 105 can couple with the pin 140 by the cams 130. A first adapter 120 coupled with a first extension 170 of the body 110 can couple with a first portion of the tensioning assembly 300 (e.g., with a connector 125, with a line 135, with a spreader bar 115, with a weight 405, or with another portion of the tensioning assembly 300) and a second adapter 120 coupled with a second extension 175 of the body 110 can couple with a second portion of the tensioning assembly 300 (e.g., with a connector 125, with a line 135, with a spreader bar 115, with a weight 405, or with another portion of the tensioning assembly). A force can be applied to at least a portion of the tensioning assembly 300 (e.g., by the weight 405, by a user pulling the tensioning assembly 300, by gravity) to cause the body 110 of the medical device to pivot at the adapters 120 to orient the body 110 from a from a first position, in which the body 110 can be resting on a portion of the patient 90 (e.g., on a patient's leg) to a second position, in which the body 110 is no longer contacting the portion of the patient 90.

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

Systems and methods described herein may be embodied in other specific forms without departing from the characteristics thereof. For example, the medical device 105 can be used with various components including, but not limited to, a femoral component, a pelvic component, a tibia component, a skeletal component, a humeral component, a shoulder component, or other various components. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

What is claimed is:

1. A medical device, comprising:
a body having a first extension and having a second extension, the first extension having a first adapter and the second extension having a second adapter;
the first adapter includes a first protrusion having a first opening and the second adapter includes a second protrusion having a second opening;
the first opening of the first adapter to couple with a first line of a tensioning assembly and the second opening of the second adapter to couple with a second line of the tensioning assembly to couple the first adapter and the second adapter with the tensioning assembly; and
the tensioning assembly to cause the body to pivot by the first adapter and the second adapter from a first position, in which the body is substantially parallel with a first position axis, to a second position, in which the body is substantially parallel with a second position axis that is at an angle relative to the first position axis.

2. The medical device of claim 1, comprising:
the first extension and the second extension extend parallel with a longitudinal axis of the body between a first end of the body and a second end of the body.

3. The medical device of claim 1, comprising:
the first line of the tensioning assembly coupled with a first connector, the first opening of the first adapter to receive a portion of the first connector to couple the first line with the first adapter; and
the second line of the tensioning assembly coupled with a second connector, the second opening of the second adapter to receive a portion of the second connector to couple the second line with the second adapter.

4. The medical device of claim 1, comprising:
the body to couple with a pin, and
the pin having a diameter in a range of 1-4 mm.

5. The medical device of claim 1, comprising:
the first adapter monolithically formed with the first extension of the body.

6. The medical device of claim 1, comprising:
the first adapter coupled with the first extension of the body by a fastener.

7. The medical device of claim 1, comprising:
the first adapter recessed into a portion of the first extension, the first adapter to extend outward from the first extension.

8. The medical device of claim 1, comprising:
the angle is in a range of 15-165 degrees between the first position axis and the second position axis.

9. The medical device of claim 1, comprising:
the first opening of the first adapter including one of a slot, a hole, or a space formed by a rod extending between two portions of the first adapter.

10. A method, comprising:
providing a medical device including a body having a first extension and having a second extension, the first extension having a first adapter, the second extension having a second adapter, the first adapter including a first protrusion having a first opening and the second adapter including a second protrusion having a second opening;
receiving, by the first opening of the first adapter, a portion of a first line of a tensioning assembly to couple the first adapter with the tensioning assembly;
receiving, by the second opening of the second adapter, a portion of a second line of the tensioning assembly to couple the second adapter with the tensioning assembly; and
applying a force to the tensioning assembly to cause the body to pivot from a first position, in which the body is substantially parallel with a first position axis, to a second position, in which the body is substantially parallel with a second position axis that is at an angle relative to the first position axis.

11. The method of claim 10, comprising:
the first extension and the second extension extend parallel with a longitudinal axis of the body between a first end of the body and a second end of the body.

12. The method of claim 10, comprising:
the first line of the tensioning assembly including a first connector, the first opening of the first adapter to receive the first line via the first connector; and
the second line of the tensioning assembly including a second connector, the second opening of the second adapter to receive the second line via the second connector.

13. The method of claim 10, comprising:
the body to couple with a pin; and
the pin having a diameter in a range of 1-4 mm.

14. The method of claim 10, comprising:
the first adapter monolithically formed with the first extension of the body.

15. The method of claim 10, comprising:
the first adapter coupled with the first extension of the body by a fastener.

16. The method of claim 10, comprising:
the first adapter recessed into a portion of the first extension, the first adapter to extend outward from the first extension.

17. The method of claim 10, comprising:
the angle is in a range of 15-165 degrees between the first position axis and the second position axis.

18. The method of claim 10, comprising:
the first opening of the first adapter including one of a slot, a hole, or a space formed by a rod extending between two portions of the first adapter.

19. An adapter, comprising:
a protrusion configured to couple with a body of a medical device;
an opening configured to receive a line of a tensioning assembly to couple with the tensioning assembly; and
the adapter to cause the body to pivot between a first position, in which the body is substantially parallel with a first position axis, to a second position, in which the body is substantially parallel with a second position axis that is at an angle relative to the first position axis, responsive to a force applied to the tensioning assembly.

20. The adapter of claim 19, comprising:

the protrusion to couple with the body of the medical device by at least one of a fastener or a tab.

* * * * *